United States Patent
Li et al.

(10) Patent No.: US 9,617,270 B2
(45) Date of Patent: Apr. 11, 2017

(54) CYTOTOXIC BENZODIAZEPINE DERIVATIVES

(71) Applicant: ImmunoGen, Inc., Waltham, MA (US)

(72) Inventors: Wei Li, Acton, MA (US); Michael Louis Miller, Framingham, MA (US); Ravi V. J. Chari, Newton, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 14/621,813

(22) Filed: Feb. 13, 2015

(65) Prior Publication Data

US 2015/0315193 A1 Nov. 5, 2015

Related U.S. Application Data

(63) Continuation of application No. PCT/US2013/055657, filed on Aug. 20, 2013.

(60) Provisional application No. 61/692,089, filed on Aug. 22, 2012.

(51) Int. Cl.
*C07D 487/04* (2006.01)
*A61K 47/48* (2006.01)

(52) U.S. Cl.
CPC ...... *C07D 487/04* (2013.01); *A61K 47/48215* (2013.01); *A61K 47/48561* (2013.01)

(58) Field of Classification Search
CPC .............. C07D 487/04; A61K 31/5517; A61K 47/48215
USPC .......................................... 540/494; 514/219
See application file for complete search history.

(56) References Cited

U.S. PATENT DOCUMENTS 8,765,740 B2    7/2014   Li et al.

FOREIGN PATENT DOCUMENTS

| WO | WO-2010/091150 A1 | 8/2010 |
| WO | WO-2012/112687 A1 | 8/2012 |

*Primary Examiner* — Deepak Rao
(74) *Attorney, Agent, or Firm* — McCarter & English, LLP; Yu Lu; Xin Zhang

(57) ABSTRACT

The invention relates to novel benzodiazepine derivatives with antiproliferative activity and more specifically to novel benzodiazepine compounds of formula (I)-(VII). The invention also provides conjugates of the benzodiazepine compounds linked to a cell-binding agent. The invention further provides compositions and methods useful for inhibiting abnormal cell growth or treating a proliferative disorder in a mammal using the compounds or conjugates of the invention.

13 Claims, 8 Drawing Sheets

FIG. 1. Scheme for Synthesis of Compounds 2-5
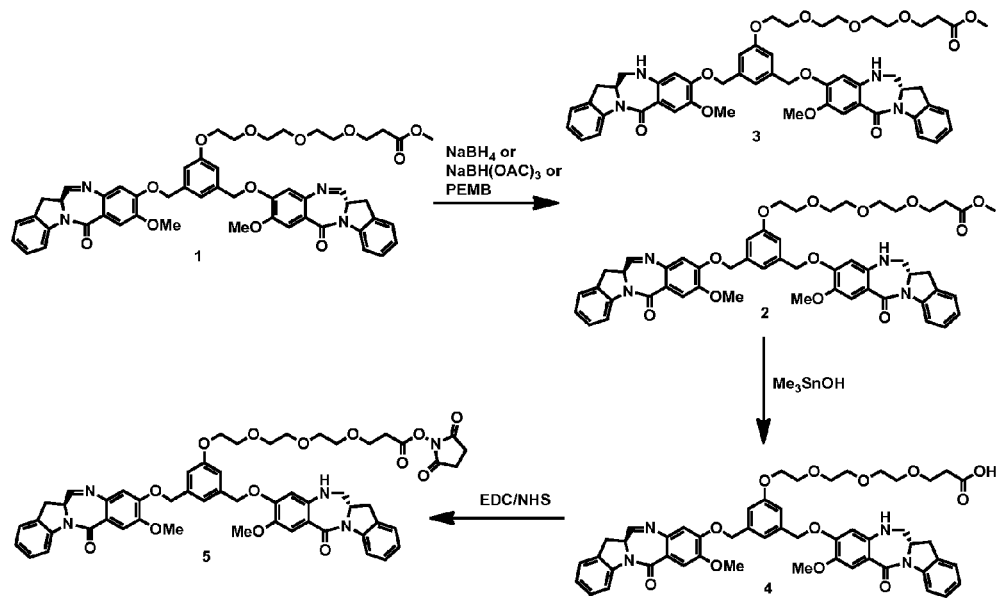
FIG. 2. Scheme for Synthesis of Compound 6
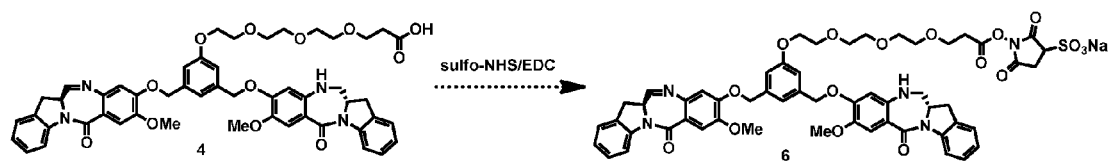
FIG. 3. Scheme for Synthesis of Compound 7
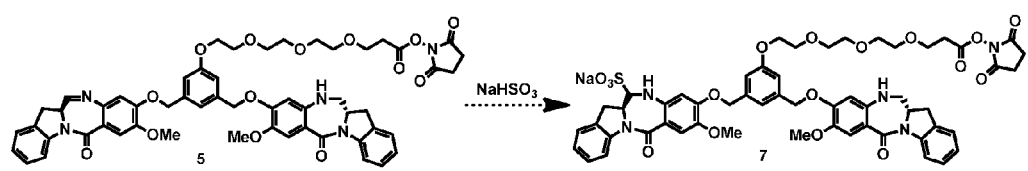

FIG. 4. Two-Step Scheme for Synthesis of Mono-Imine Compounds 2 and 15
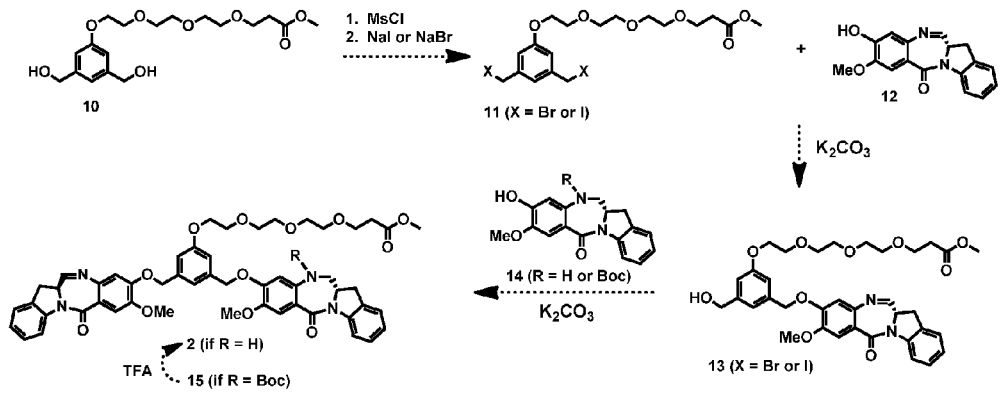
FIG. 5. One-Step Scheme for Synthesis of Compound 16
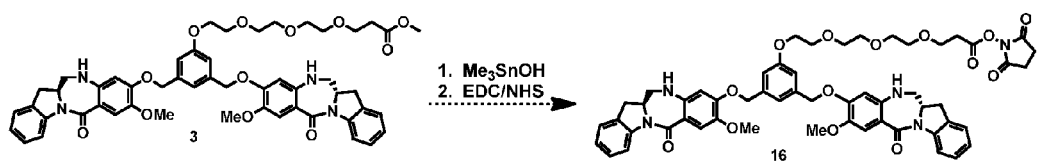
FIG. 6. One-Step Scheme for Synthesis of Compounds 21 and 19
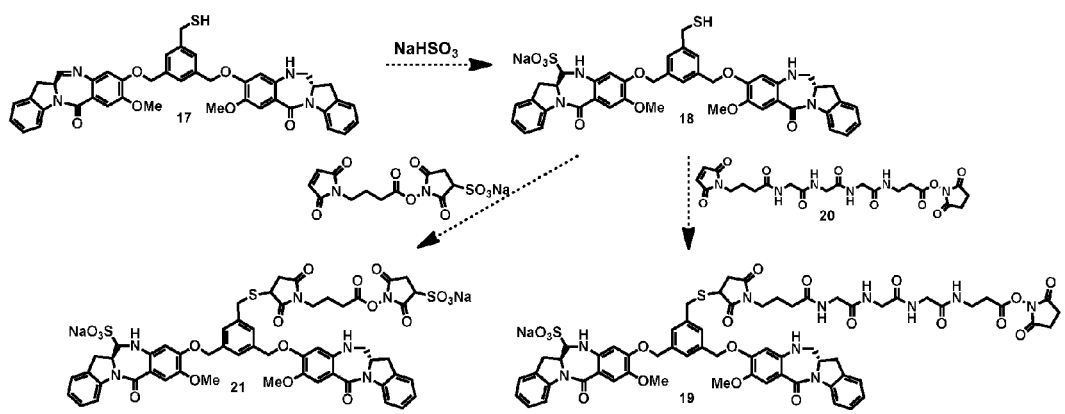

FIG. 7. One-Step Scheme for Synthesis of Conjugates 22-24
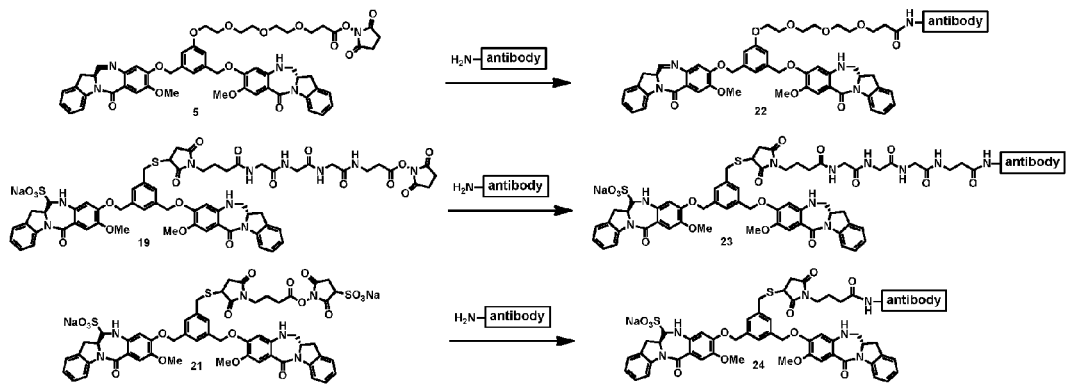
FIG. 8. Antiproliferative Activity of Compound 2 against Namalwa, KB, and HL60/QC Cell Lines
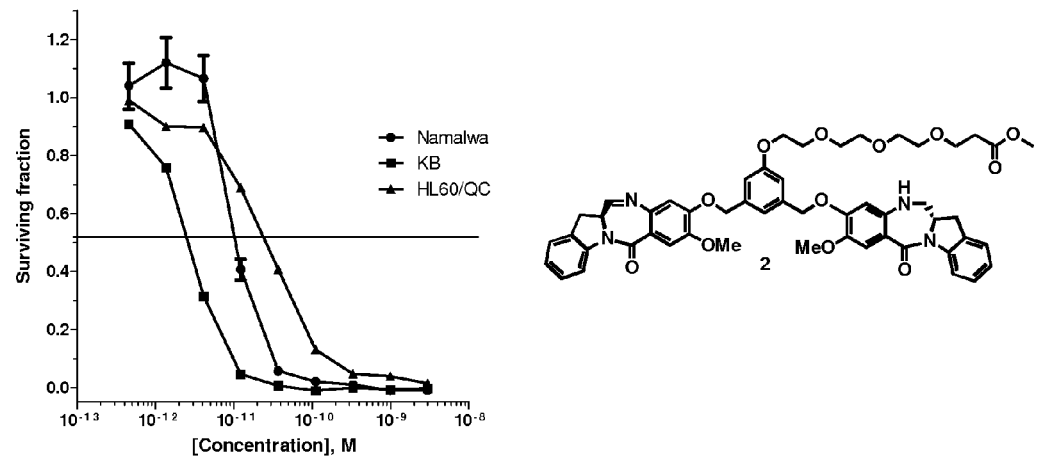

FIG. 9. Antiproliferative Activity of Conjugate 22 against A) HL60/QC Cells with and without Blocking of Antigen Binding Site, B) NB4 Cells, and C) HEL92.1.7 Cells.

FIG. 10. Antiproliferative Activity of Conjugate 24 against A) HL60/QC cells with and without Blocking of Antigen Binding Site, B) NB4 Cells, and C) HEL92.1.7 Cells.

FIG. 11. Antiproliferative Activity of Conjugate 23 against A) HL60/QC Cells with and without Blocking of Antigen Binding Site, B) NB4 Cells, and C) HEL92.1.7 Cells.

FIG. 12. Synthetic Scheme of One-Step Linkable Dimers 34-35
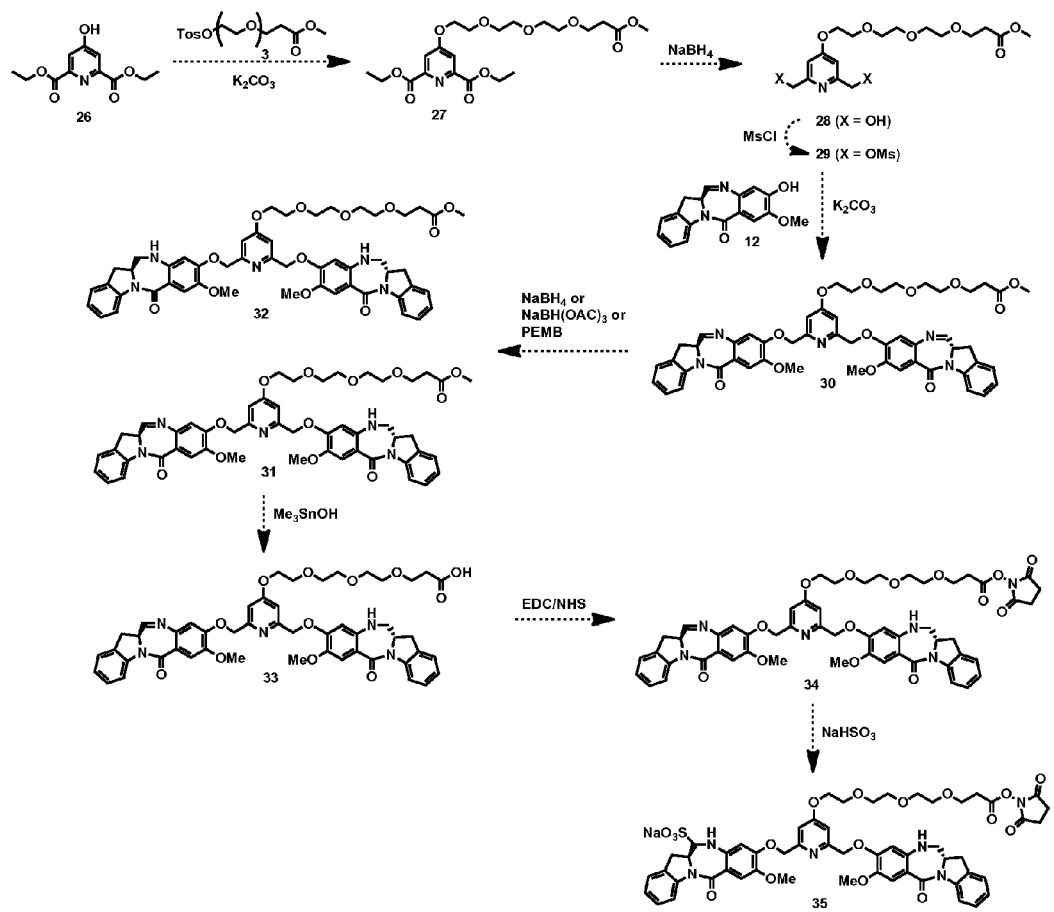
FIG. 13. Synthetic Scheme of One-Step Linkable Dimer 36
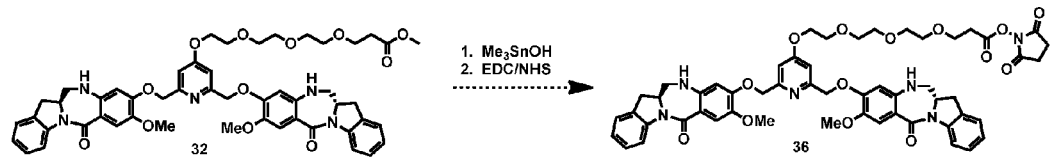

FIG. 14. Synthetic Scheme of One-Step Linkable Dimers 44-45
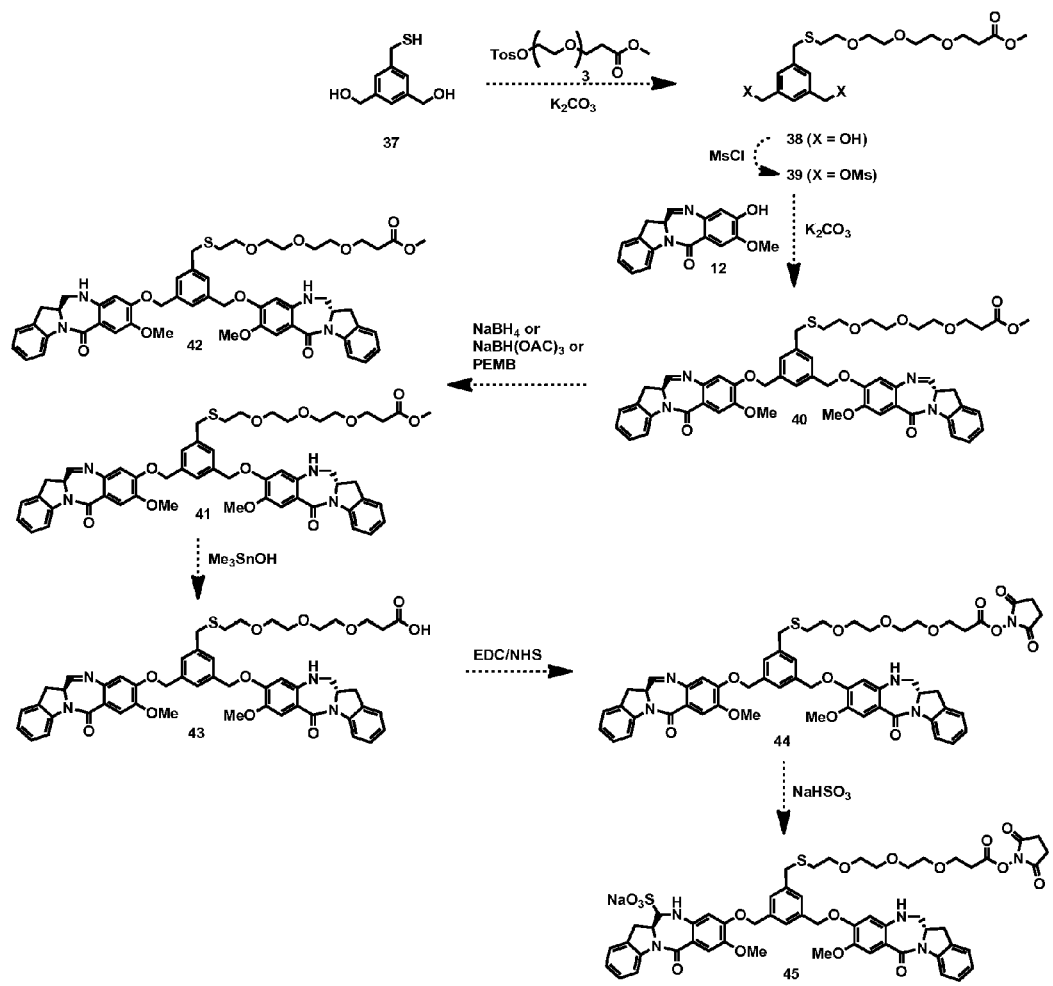
FIG. 15. Synthetic Scheme of One-Step Linkable Dimer 46
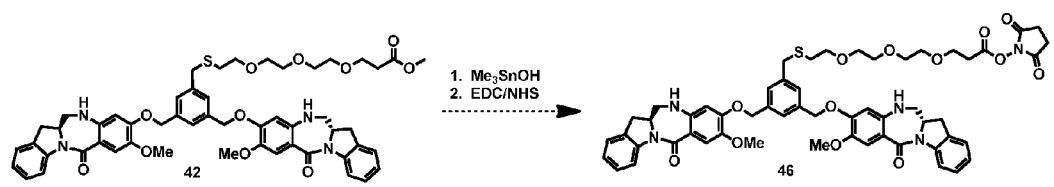

CYTOTOXIC BENZODIAZEPINE DERIVATIVES

REFERENCE TO RELATED APPLICATION

This application is a continuation application of International Patent Application No. PCT/US2013/055657, filed on Aug. 20, 2013; which claims the benefit of the filing date of U.S. Provisional Application No. 61/692,089, filed on Aug. 22, 2012. All of the above-referenced applications are incorporated by reference in their entirety.

FIELD OF THE INVENTION

The present invention relates to novel cytotoxic compounds, and cytotoxic conjugates comprising these cytotoxic compounds and cell-binding agents. More specifically, this invention relates to novel benzodiazepine compounds, derivatives thereof, intermediates thereof, conjugates thereof, and pharmaceutically acceptable salts thereof, which are useful as medicaments, in particular as antiproliferative agents.

BACKGROUND OF THE INVENTION

Benzodiazepine derivatives are useful compounds for treating various disorders, and include medicaments such as, antiepileptics (imidazo[2,1-b][1,3,5]benzothiadiazepines, U.S. Pat. No. 4,444,688; U.S. Pat. No. 4,062,852), antibacterials (pyrimido[1,2-c][1,3,5]benzothiadiazepines, GB 1476684), diuretics and hypotensives (pyrrolo(1,2-b)[1,2,5] benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

Recently, it has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo[1,2-b][1,2,5]benzothiadiazepines and pyrrolo[1,2-b][1,2,5]benzodiazepine derivatives (WO 2007/015280), tomaymycin derivatives (e.g., pyrrolo [1,4]benzodiazepines), such as those described in WO 2000/12508, WO 2005/085260, WO 2007/085930, and EP 2019104. Benzodiazepines are also known to affect cell growth and differentiation (Kamal A., et al., *Bioorg. Med. Chem.* 2008 Aug. 15, 16(16):7804-7810 (and references cited therein); Kumar R, *Mini Rev. Med. Chem.* 2003 June, 3(4):323-339 (and references cited therein); Bednarski J J, et al., 2004; Sutter A. P, et al., 2002; Blatt N B, et al., 2002); Kamal A. et al., *Current Med. Chem.*, 2002, 2:215-254; Wang J-J., *J. Med. Chem.*, 2206, 49:1442-1449; Alley M. C. et al., *Cancer Res.* 2004, 64:6700-6706; Pepper C. *J. Cancer Res* 2004, 74:6750-6755; Thurston D. E. and Bose D. S., *Chem. Rev.* 1994, 94:433-465; and Tozuka, Z., et al., *Journal of Antibiotics*, (1983) 36:1699-1708. General structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove and crosslink DNA enables them to interfere with DNA processing, hence their potential for use as antiproliferative agents.

The first pyrrolobenzodiazepine to enter the clinic, SJG-136 (NSC 694501) is a potent cytotoxic agent that causes DNA inter-strand crosslinks (S. G Gregson et al., 2001, *J. Med. Chem.*, 44: 737-748; M. C. Alley et al., 2004, *Cancer Res.*, 64:6700-6706; J. A. Hartley et al., 2004, *Cancer Res.*, 64: 6693-6699; C. Martin et al., 2005, *Biochemistry*, 44: 4135-4147; S. Arnould et al., 2006, *Mol. Cancer Ther.*, 5:1602-1509). Results from a Phase I clinical evaluation of SJG-136 revealed that this drug was toxic at extremely low doses (maximum tolerated dose of 45 µg/m$^2$, and several adverse effects were noted, including vascular leak syndrome, peripheral edema, liver toxicity and fatigue. DNA damage was noted at all doses in circulating lymphocytes (D. Hochhauser et al., 2009, *Clin. Cancer Res.*, 15: 2140-2147). Thus, there exists a need for improved benzodiazepine derivatives that are less toxic and still therapeutically active for treating a variety of proliferative disease states, such as cancer.

SUMMARY OF THE INVENTION

Cytotoxic benzodiazepine dimers disclosed in the art possess two imine functionalities in their free form or reversibly protected form, such as a hydrate, alkoxylate or sulfonate. The presence of these two imine functionalities results in crosslinking of DNA (S. G. Gregson et al., 2001, *J. Med. Chem.*, 44: 737-748). The present invention is partly based on the unexpected finding that cell binding agent-conjugates of new cytotoxic benzodiazepine derivatives, such as indolinobenzodiazapene dimers that has one or no imine functionality, and thus incapable of crosslinking DNA, display a much higher therapeutic index (ratio of maximum tolerated dose to minimum effective dose) in vivo compared to benzodiazepine derivatives that can crosslink DNA that are previously disclosed in the art.

One aspect of this invention features a cytotoxic compound represented by CM-Q or CM'-Q'. CM and CM' are each a cytotoxic moiety, and Q and Q' are each a reactive group that can form a covalent bond with a cell binding agent (CBA).

In one embodiment, CM is represented by any one of the following formulas:

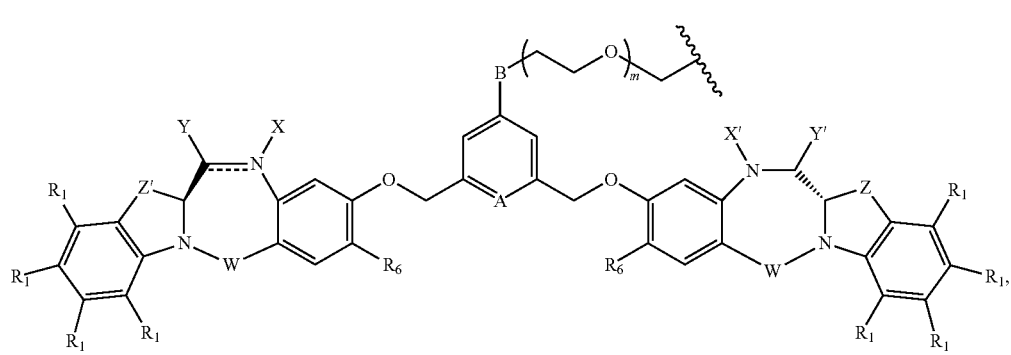

I

-continued
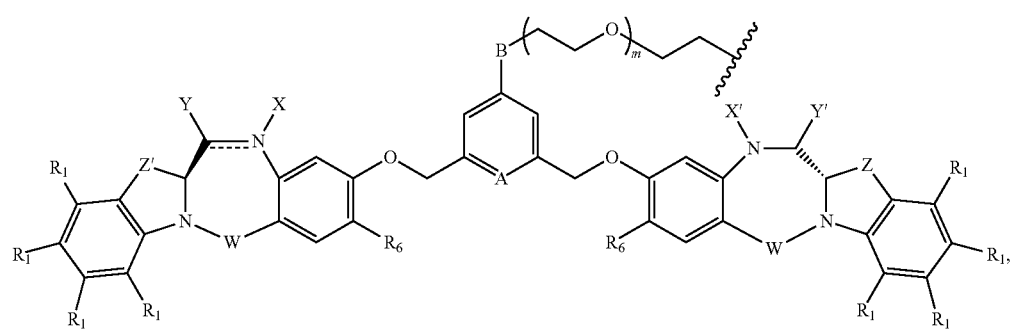
I'
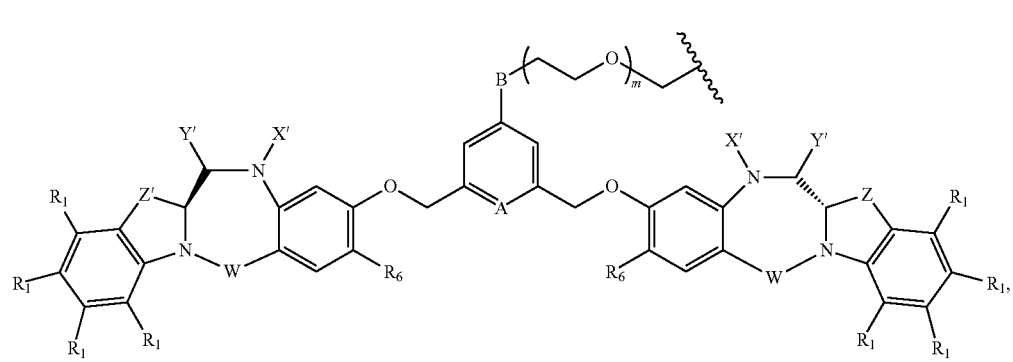
II
II'
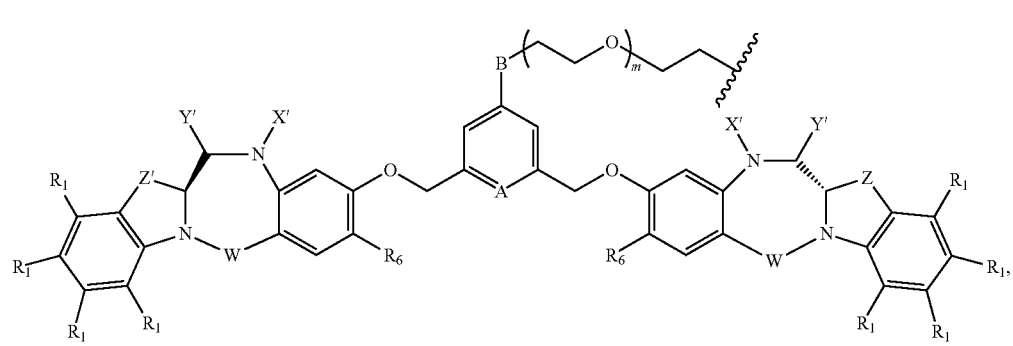
III
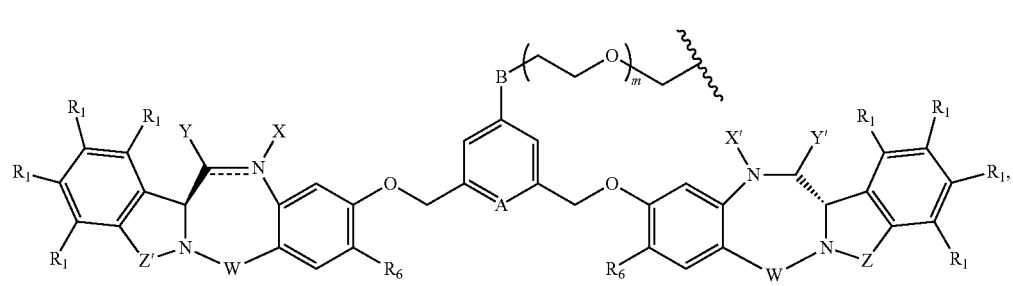
III'
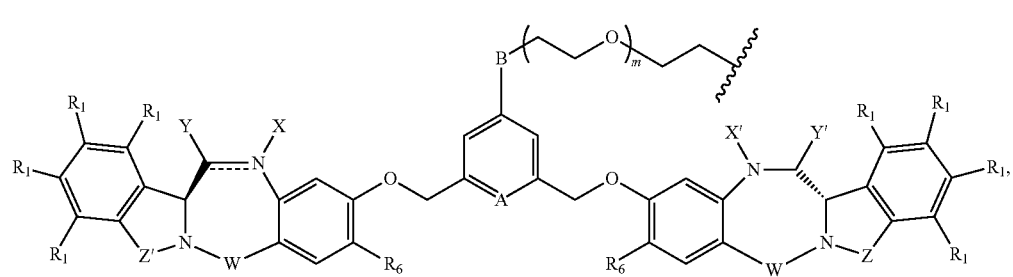

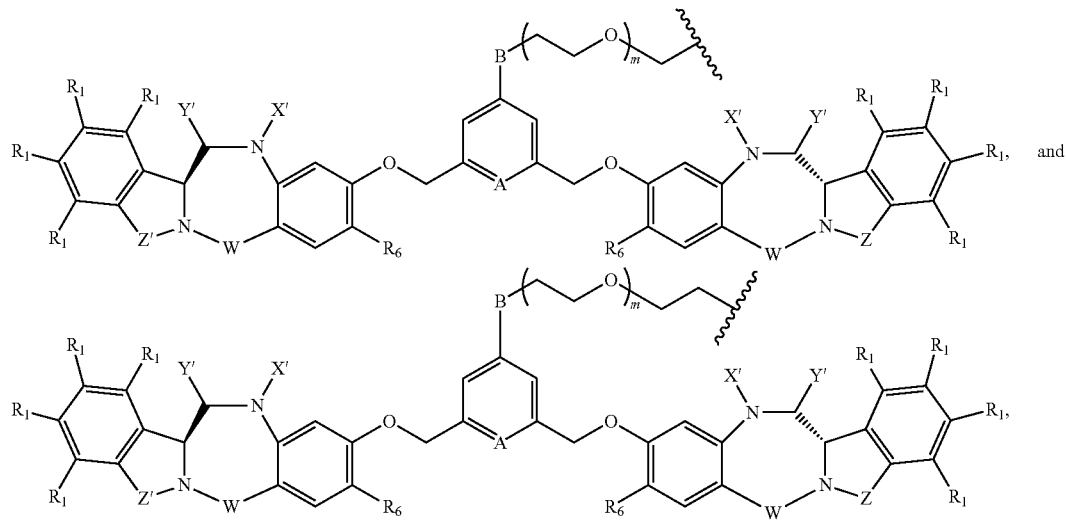

IV or a pharmaceutically acceptable salt thereof, wherein:
A is CH or N;
B is O— or CH$_2$—S—;
Q is a reactive group that can form a covalent bond with a cell binding agent (CBA). In one embodiment, Q is selected from the group consisting of a maleimide, a haloacetamido, —SH, —SSR$^d$, —CH$_2$SH, —CH(Me)SH, —C(Me)$_2$SH, —NHR$^{c1}$, —ArNHR$^{c1}$, —CH$_2$NHR$^{c1}$, —NR$^{c1}$NH$_2$, —COOR$^e$, and —COE, wherein —COE represents a reactive ester selected from, but not limited to, the group consisting of N-hydroxysuccinimide ester, N-hydroxy sulfosuccinimide ester, nitrophenyl ester, dinitrophenyl ester, sulfo-tetrafluorophenyl ester, and pentafluorophenyl ester, wherein R$^{c1}$ is —H or a substituted or unsubstituted linear or branched alkyl having 1 to 4 carbon atoms, R$^d$ is selected from the group consisting of phenyl, nitrophenyl, dinitrophenyl, carboxynitrophenyl, pyridyl and nitropyridyl; Ar is an aryl or a heteroaryl; and alternatively, Q is —C(=O)OH, —C(=O)OMe, or

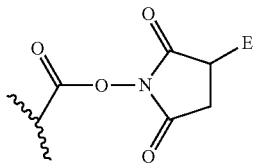

and E is —H or —SO$_3$H. In one embodiment, Ar is phenyl.
the double line $=$ between N and C represents a single bond or a double bond, provided that when the double line $=$ is a double bond, X is absent and Y is —H, a linear C1-C4 alkyl or a branched C1-C4 alkyl; and when the double line $=$ is a single bond, X is —H or an amine protecting moiety and Y is selected from the group consisting of —H, —OR, —OCOR', —OCOOR', —OCONR'R", —NR'R", —NR'COR", —NR'NR'R", an optionally substituted 5- or 6-membered nitrogen-containing heterocycle, a guanidinum represented by —NR'(C=NH)NR'R", an amino acid, or a peptide represented by —NRCOP', wherein P' is an amino acid or a polypeptide containing between 2 to 20 amino acid units, —SR, —SOR', —SO$_2$H, —SO$_3$H, —OSO$_3$H, halogen, cyano, an azido, a sulfite, a meta-bisulfite, a mono-, di-, tri-, and tetra-thiophosphate, a thio phosphate ester R$^i$S—, R$^i$SO, R$^i$SO$_2$, R$^i$SO$_3$, thiosulfate, dithionite, a phosphorodithioate, a hydroxamic acid, and formaldehyde sulfoxylate, wherein R$^i$ is a linear C1-C10 alkyl or a branched C1-C10 alkyl and is substituted with at least one substituent selected from the group consisting of —N(R$^j$)$_2$, —CO$_2$H, —SO$_3$H, and —PO$_3$H, R$^i$ can be further optionally substituted with an alkyl described herein, R$^j$ is a linear C1-C6 alkyl or a branched C1-C6 alkyl, R$^{k'}$ is a linear C1-C10 alkyl, a branched C1-C10 alkyl, a cyclic C3-C10 alkyl, a linear C2-C10 alkenyl, a branched C2-C10 alkenyl, a cyclic C3-C10 alkenyl, a linear C2-C10 alkynyl, a branched C2-C10 alkynyl, a cyclic C3-C10 alkynyl, aryl, heterocyclyl or heteroaryl;

R, for each occurrence, is independently selected from the group consisting of —H, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from the group consisting of nitrogen, oxygen, and sulfur, and an optionally substituted 3- to 18-membered heterocyclic ring containing 1 to 6 heteroatoms independently selected from the group consisting of O, S, N and P;

R' and R" are each independently selected from the group consisting of —H, —OH, —OR, —NHR, —NR$_2$, —COR, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, a polyethylene glycol unit —(CH$_2$CH$_2$O)$_n$—R$^c$, and an optionally substituted 3- to 18-membered heterocyclic ring having 1 to 6 heteroatoms independently selected from the group consisting of O, S, N and P;

R$^c$ is —H, an optionally substituted linear C1-C4 alkyl or an optionally substituted branched C1-C4 alkyl;

n is an integer from 1 to 24;

W is selected from the group consisting of C=O, C=S, CH$_2$, BH, SO and SO$_2$;

X', for each occurrence, is independently selected from the group consisting of —H, an amine-protecting group, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from the group consisting of nitrogen, oxygen, and sulfur, and an optionally substituted 3- to 18-membered heterocyclic ring containing 1 to 6 heteroatoms independently selected from the group consisting of O, S, N and P;

Y', for each occurrence, is independently selected from the group consisting of —H, an oxo group, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, an optionally substituted 6- to 18-membered aryl, an optionally substituted 5- to 18-membered heteroaryl ring containing one or more heteroatoms independently selected from the group consisting of nitrogen, oxygen, and sulfur, and an optionally substituted 3- to 18-membered heterocyclic ring having 1 to 6 heteroatoms;

R$_1$, for each occurrence, is independently selected from the group consisting of —H, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3$H, a sulfate —OSO$_3$H, a sulfonamide represented by —SO$_2$NR'R", cyano, an azido, —COR', —OCOR', and —OCONR'R";

R$_6$ is selected from the group consisting of —H, —R, —OR, —SR, —NR'R", —NO$_2$, and halogen;

Z and Z' are each independently selected from the group consisting of —(CH$_2$)$_{n'}$—, —(CH$_2$)$_{n'}$—CR$_7$R$_8$—(CH$_2$)$_{n'}$—, —(CH$_2$)$_{n'}$—NR$_9$—(CH$_2$)$_{n'}$—, —(CH$_2$)$_{n'}$—O—(CH$_2$)$_{n'}$— and —(CH$_2$)$_{n'}$—S—(CH$_2$)$_{n'}$—;

n', for each occurrence, is independently 0 or an integer of 1, 2 or 3;

R$_7$ and R$_8$ are the same or different, and are each independently selected from the group consisting of —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear C1-C10 alkyl, an optionally substituted branched C1-C10 alkyl, and an optionally substituted cyclic C3-C10 alkyl;

R$_9$ is independently selected from the group consisting of —H, an optionally substituted linear C1-C10 alkyl, an optionally substituted branched C1-C10 alkyl, and an optionally substituted cyclic C3-C10 alkyl, and a polyethylene glycol unit —(OCH$_2$CH$_2$)$_n$—;

m is an integer from 1 to 24.

In one embodiment, CM' is represented by any one of the following formulas:

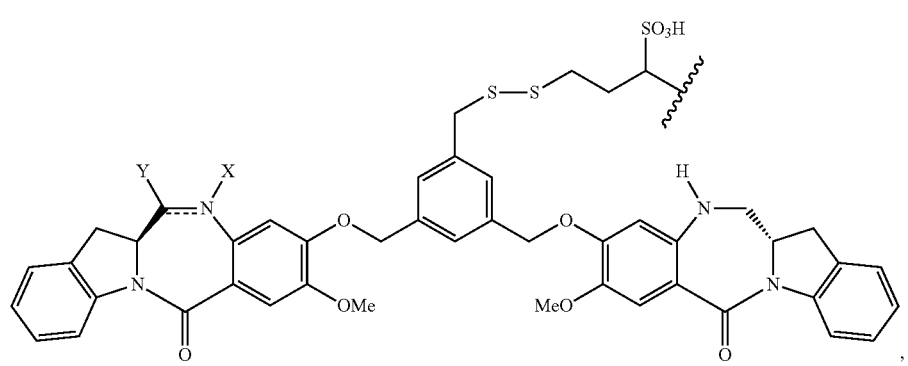

V

-continued

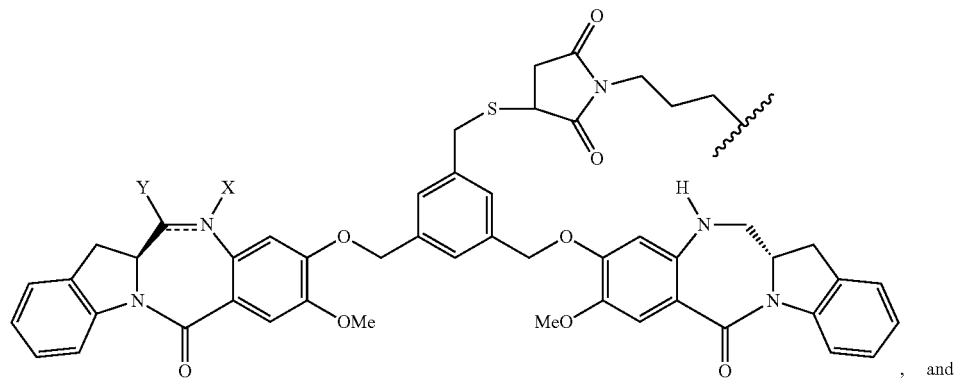

VI

, and

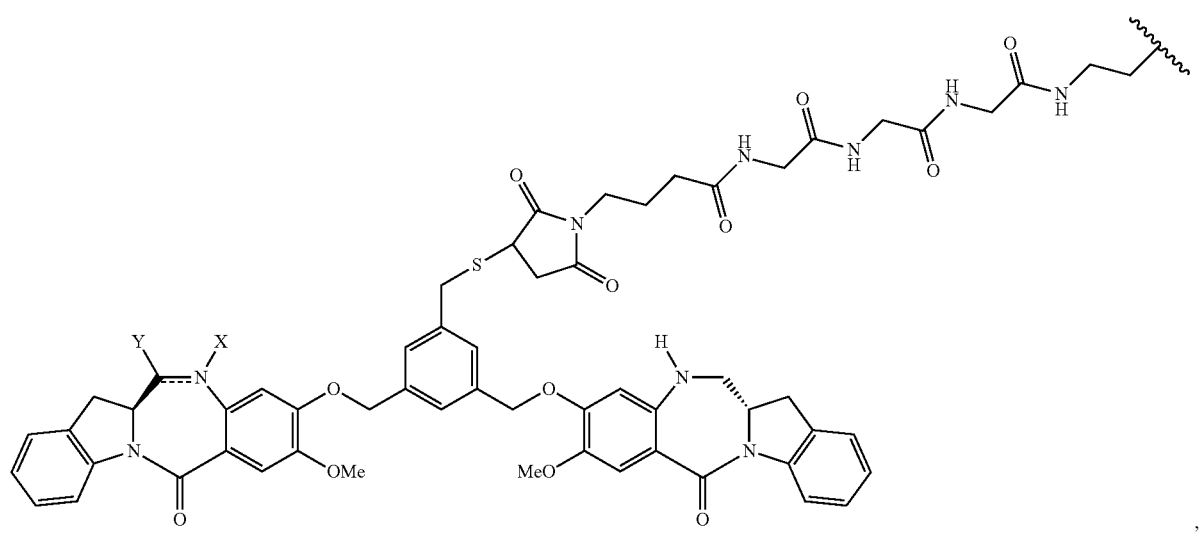

VII

, or a pharmaceutically acceptable salt thereof, wherein the double line ⹀ between N and C represents a single bond or a double bond, provided that when it is a double bond, X is absent and Y is —H; and when it is a single bond, X is —H and Y is —SO₃H.

For Formulas V-VII, Q' is a reactive group that can form a covalent bond with a cell binding agent (CBA). Alternatively, Q' is selected from the group consisting of a maleimide, a haloacetamido, —SH, —SSR$^d$, —CH₂SH, —CH(Me)SH, —C(Me)₂SH, —NHR$^{c1}$, —ArNHR$^{c1}$, —CH₂NHR$^{c1}$, —NR$^{c1}$NH₂, —COOR$^e$, and —COE, wherein —COE represents a reactive ester selected from, but not limited to, the group consisting of N-hydroxysuccinimide ester, N-hydroxy sulfosuccinimide ester, nitrophenyl ester, dinitrophenyl ester, sulfo-tetrafluorophenyl ester, and pentafluorophenyl ester, wherein R$^{c1}$ is —H or a substituted or unsubstituted linear or branched alkyl having 1 to 4 carbon atoms, and R$^d$ is selected from the group consisting of phenyl, nitrophenyl, dinitrophenyl, carboxynitrophenyl, pyridyl and nitropyridyl, Ar is an aryl or a heteroaryl; and P is an amino acid or a peptide comprising 2 to 20 amino acids. In yet another alternative, Q' is —C(=O)OH, —C(=O)OMe, or

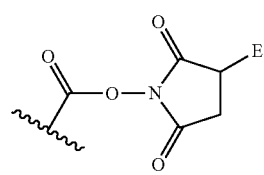

and E is —H or —SO₃H. In one embodiment, Ar is phenyl.

In another aspect, this invention features a conjugate comprising a cytotoxic moiety (i.e., CM or CM') represented by any one of formulas I-VII and a CBA. Specifically, the conjugate is represented by any one of the following formulas:

$$\left[ CM-\overset{O}{\overset{\|}{C}}-\underset{H}{N}\sim CBA \right]_r ;$$

(IX)

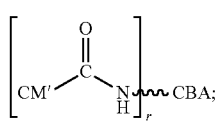
(X)

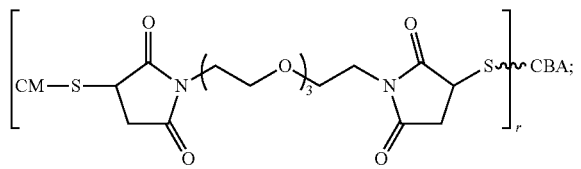

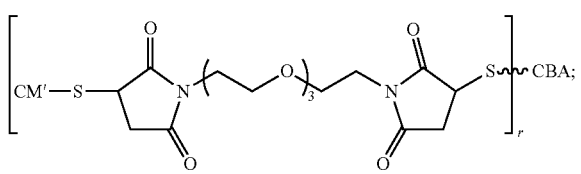

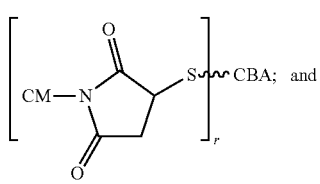

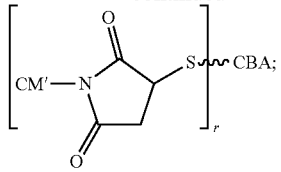

wherein r is an integer from 1 to 10.

In a conjugate of Formula IX or X, the CBA binds to specific target cells, such as tumor cells, virus infected cells, microorganism infected cells, parasite infected cells, auto-immune cells, activated cells, myeloid cells, activated T-cells, B cells, melanocytes, or cells expressing CD4, CD6, CD19, CD20, CD22, CD30, CD33, CD37, CD38, CD40, CD44, CD56, EpCAM, CanAg, CALLA, Her-2 antigens, Her-3 antigens, insulin growth factor receptor, epidermal growth factor receptor, and/or folate receptor.

Examples of the CBA may include an antibody, a single chain antibody, an antibody fragment, a polyclonal antibody, a monoclonal antibody, a single chain monoclonal antibody, a monoclonal antibody fragment, a chimeric antibody, a chimeric antibody fragment, a domain antibody, a domain antibody fragment, a lymphokine, a hormone, a vitamin, a growth factor, a colony stimulating factor, or a nutrient-transport molecule. The antibody can be a monoclonal antibody or a humanized antibody. Illustrative examples of the antibody include huMy9-6, huFOLR1, and chB38.1.

In one embodiment, CM in the conjugate represented by Formula IX is not the following cytotoxic moiety:

XI

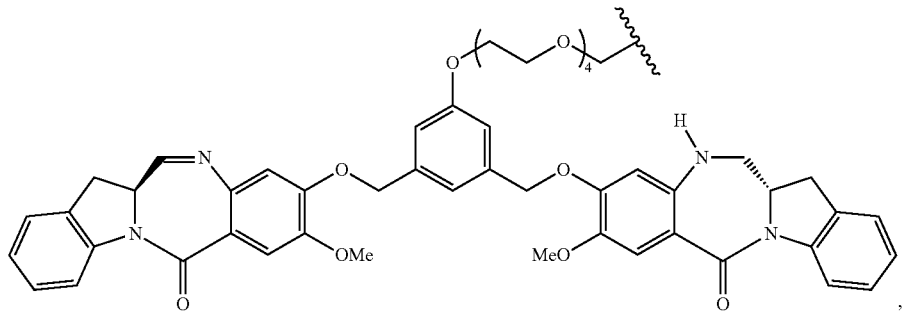

and/or a salt thereof.

In still another aspect, the invention features a cytotoxic compound represented by the following formula:

XII

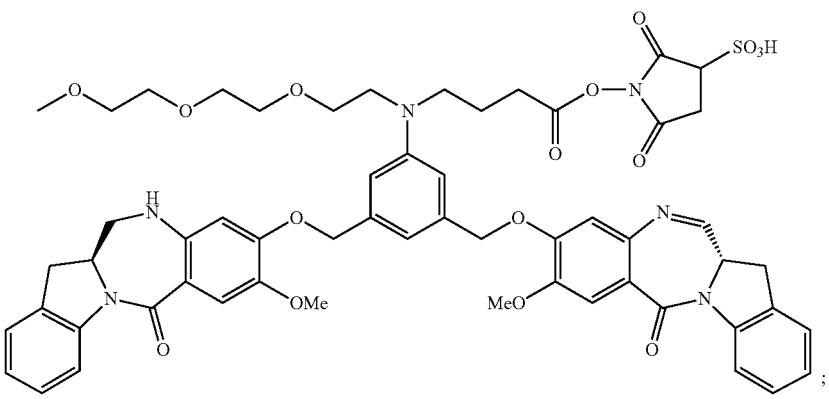

or a pharmaceutically acceptable salt thereof.

Also within the scope of this invention is a composition (e.g., a pharmaceutical composition) comprising a benzodiazepine compound having CM or CM' represented by any one of Formulas I-VII, a benzodiazepine compound represented by Formula XII, a conjugate represented by Formula IX or X, or a pharmaceutical acceptable salt thereof, except for the conjugate having CM represented by Formula XI and/or a salt thereof. The composition may also include a carrier (e.g., a pharmaceutically acceptable carrier). The composition can further include a second therapeutic agent.

The present invention also includes a method of inhibiting abnormal cell growth or treating a proliferative disorder, an autoimmune disorder, graft versus host disease, transplant rejection, immune deficiency, inflammatory diseases, destructive bone disorder, infectious disease, viral disease, fibrotic disease, neurodegenerative disorder, or kidney disease in a mammal (e.g., human), comprising administering to said mammal a therapeutically effective amount of a benzodiazepine compound represented by any one of Formulas I-VII and XII, a conjugate represented by Formula IX or X (except for the conjugate having CM represented by Formula XI), a solvate thereof, a hydrate thereof, or a pharmaceutical acceptable salt thereof.

In a specific embodiment, the method described above further comprises administering to said mammal sequentially or consecutively a second therapeutic agent.

BRIEF DESCRIPTION OF THE FIGURES

FIGS. 1, 2, 3, 4, 5 and 6 show the schemes for synthesis of representative benzodiazepine compounds suitable for preparation of conjugates encompassed by the present invention.

FIG. 7 shows the scheme for one-step synthesis of representative antibody-benzodiazepine compound conjugates.

FIG. 8 shows the in vitro antiproliferative activity of compound 2 against Namalwa, KB and HL60/QC cell lines.

FIGS. 10A, 9B and 9C show the in vitro antiproliferative activity of conjugate 24 against cell lines HL60/QC (with or without the blocking antigen binding site), NB4 (without the blocking antigen binding site) and HEL92.1.7 (without the blocking antigen binding site), respectively.

FIG. 12 is a synthetic scheme of One-Step Linkable Dimers 34-35.

FIG. 13 is a synthetic scheme of One-Step Linkable Dimer 36.

FIG. 14 is a synthetic scheme of One-Step Linkable Dimers 44-45.

FIG. 15 is a synthetic scheme of One-Step Linkable Dimer 46.

DETAILED DESCRIPTION OF THE INVENTION

Figure 9A:
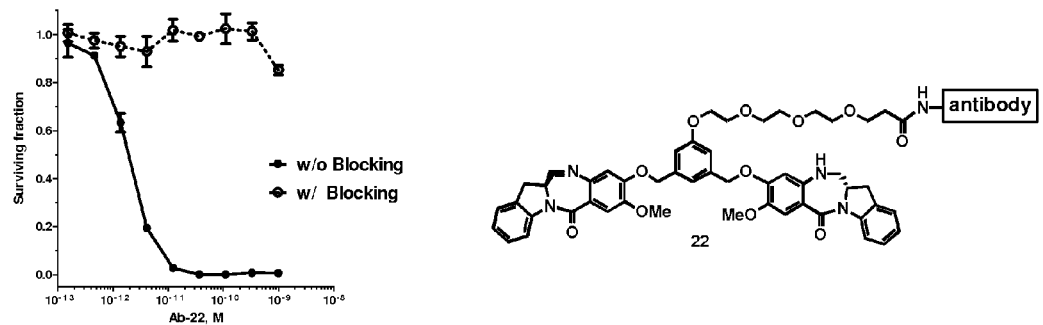
FIGS. 9A, 9B and 9C show the in vitro antiproliferative activity of conjugate 22 against cell lines HL60/QC (with or without the blocking antigen binding site), NB4 (without the blocking antigen binding site) and HEL92.1.7 (without the blocking antigen binding site), respectively.
Figure 9B:
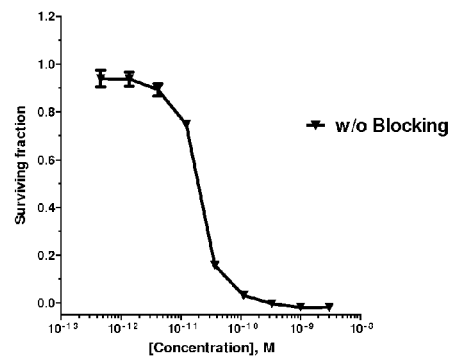
Figure 9C:
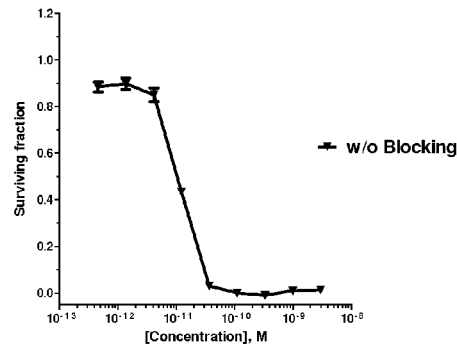

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

DEFINITIONS

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6], or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A series of Monographs* (John Wiley & Sons, New York, 1950 to present), in particular Volumes 13, 14, 16, 19, and 28; and *J. Am. Chem. Soc.* (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or Ο-carboline.

The heteroatoms present in heteroaryl or heterocycicyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyicyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocycycl, —SR$^{101}$, —SOR$^{101}$, —SO$_2$R$^{101}$ and —SO$_3$M.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, and salts (e.g., pharmaceutically acceptable salts) of all the formulae disclosed in the present invention. The term also includes any solvates, hydrates, and polymorphs of any of the foregoing. The specific recitation of "stereoisomers," "geometric isomers," "tautomers," "solvates," "salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds*, John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

One preferred form of the compound of the invention includes compounds (with or without any linker groups) and conjugates of the invention comprising an adduct formed between an imine bond of the compounds/conjugates and an imine reactive reagent. Another preferred form of the compound of the invention includes compounds such as those of formula (I)-(IV), wherein when the double line == between N and C represents a single bond, X is H or an amine protecting group. A compound of the invention may contain one or both forms described herein (e.g., containing an adduct formed between an imine bond of the compounds/conjugates and an imine reactive reagent, and/or containing a Y leaving group when X is —H).

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, head/brain and neck cancer, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

A "therapeutic agent" encompasses both a biological agent such as an antibody, a peptide, a protein, an enzyme or a chemotherapeutic agent.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, Ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

Chemotherapeutic agents may also include any of the generic drugs or biosimilars of the brand-name drugs referenced herein, or improvements thereof, including improved formulations, delivery means (sustained release, bioadhesive coating, targeted delivery etc.), and dosage forms.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, *Protective Groups in Organic Synthesis*, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, *Protective Groups in Organic Synthesis*, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "reactive group" refers to a group that can form a covalent bond with a cell binding agent. More specifically, it reacts with an amino group on a lysine residue or a thiol group on a cysteine residue to form a covalent link between CM and a CBA.

The term "amino acid" refers to naturally occurring amino acids or non-naturally occurring amino acid represented by $NH_2$—$C(R^{aa'}R^{aa})$—$C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl. The term "amino acid" also refers to the corresponding residue when one hydrogen atom is removed from the amine and/or carboxy end of the amino acid, such as —NH—C$(R^{aa'}R^{aa})$—C(=O)O—.

The term "cation" refers to an ion with positive charge. The cation can be monovalent (e.g., $Na^+$, $K^+$, etc.), bi-valent (e.g., $Ca^{2+}$, $Me^+$, etc.) or multi-valent (e.g., $Al^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cytotoxic Compounds

In one aspect, the present invention is related to cytotoxic compounds, each of which contains a cytotoxic moiety (CM or CM') represented by any one of Formulas I-VII; and a cytotoxic compound represented by Formula XII.

In a first specific embodiment, in Formulas I-IV, A is —CH— and B is —O—; A is —N— and B is —O—; or A is —CH— and B is —CH$_2$—S—, and the remainder of the variables are as defined in Formulas I-IV.

In a second specific embodiment, for Formulas I and III, the double line ⚌ between N and C represents a single bond or a double bond, provided that when the double line ⚌ is a double bond, X is absent and Y is —H, or a linear C1-C4 alkyl or a branched C1-C4 alkyl; and when the double line ⚌ is a single bond, X is —H, or an amine protecting moiety, and Y is selected from the group consisting of —H, —OR, —OCOR', —OCOOR', —OCONR'R", —NR'R", —NR'COR", —NR'NR'R", an optionally substituted 5- or 6-membered nitrogen-containing heterocycle, a guanidinum represented by —NR'(C=NH)NR'R", an amino acid, and a peptide represented by —NRCOP', wherein P' is an amino acid or a polypeptide containing between 2 to 20 amino acid units, —SR, —SOR', —SO$_2$H, —SO$_3$H, —OSO$_3$H, halogen, cyano, and an azido; and the reminder of the variables are as defined for Formulas I-IV or the first specific embodiment.

In a third specific embodiment, in Formula I, II, III, or IV, CM is represented by any one of the following formulas:

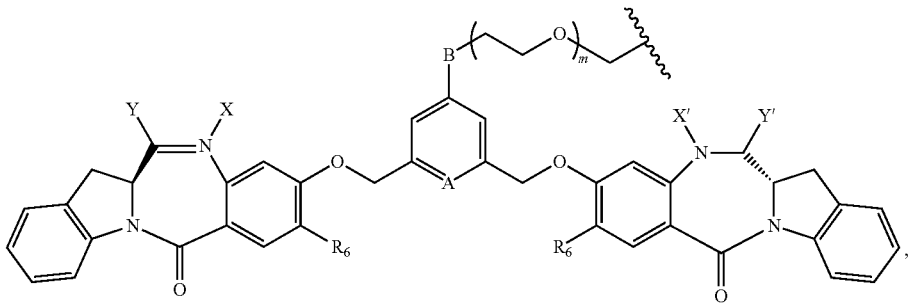

XIII

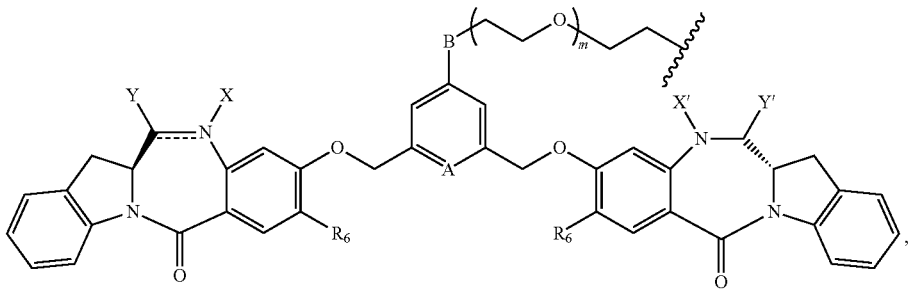

XIII'

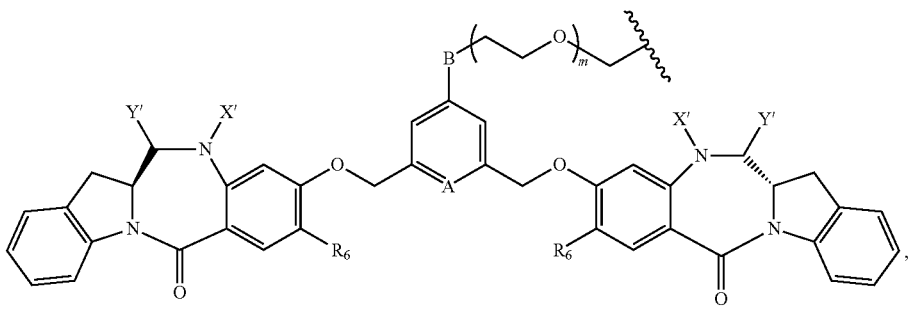

XIV

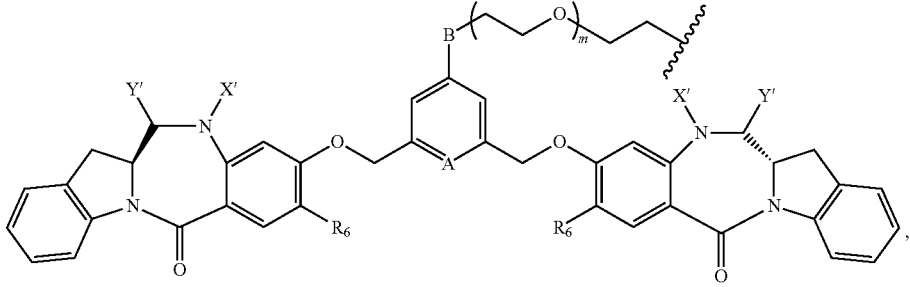

XIV'

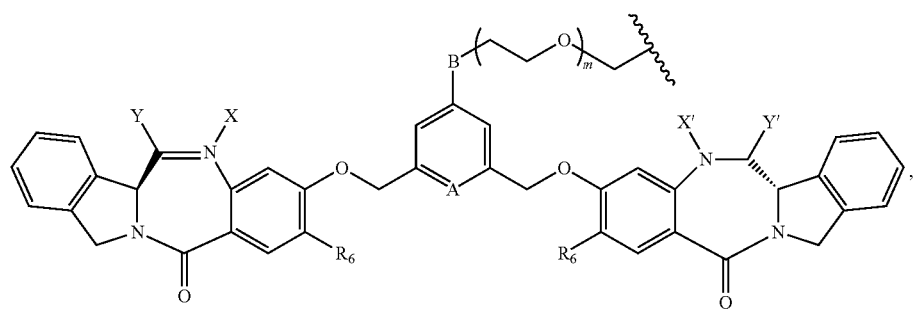

XV

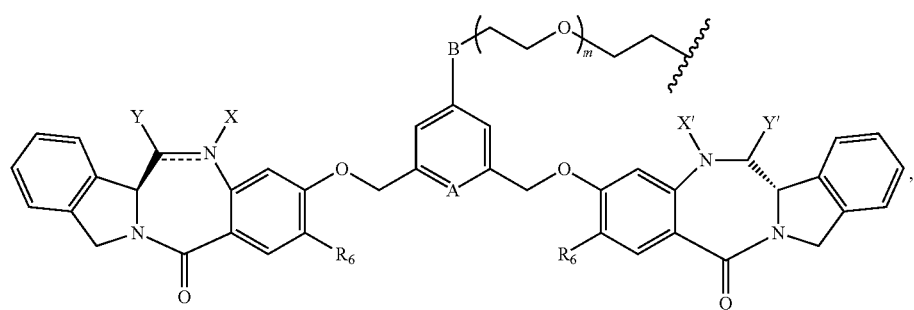

XV'

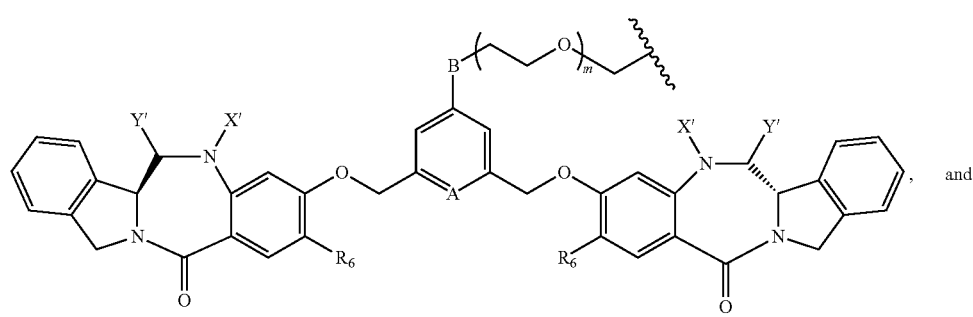

XVI

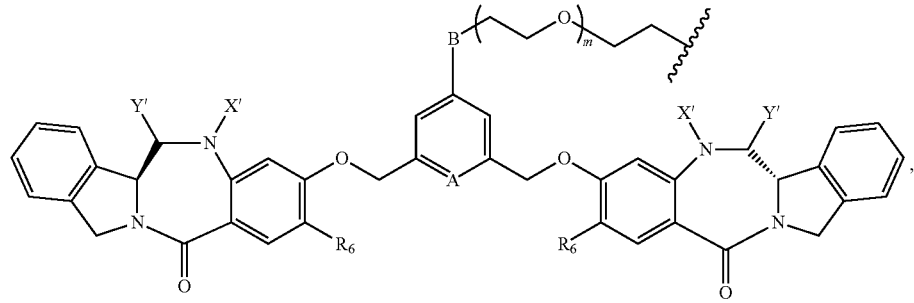

, wherein variables are as defined for Formulas I-IV or first or second specific embodiment.

Alternatively, in Formulas XIII-XVI, the double line ⚌ between N and C represents a single bond or a double bond, provided that when the double line ⚌ is a double bond, X is absent and Y is —H; and when the double line ⚌ is a single bond, X is —H or the amine protecting group and Y is selected from the group consisting of —H, —OR, —OCOR', —SR, —NR'R", —SO$_3$H, —SO$_2$H and —OSO$_3$H;

R is independently selected from the group consisting of —H, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, and a PEG group —(CH$_2$CH$_2$O)$_n$—R$^c$, wherein n is an integer from 1 to 24, and R$^c$ is a linear C1-C4 alkyl or a branched C1-C4 alkyl;

R' and R" are each independently selected from the group consisting of —H, —OH, —OR, —NRR$^{g'}$, —COR, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, an optionally substituted aryl having from 6 to 18 carbon atoms, and an optionally substituted 3- to 18-membered heterocyclic ring having 1 to 6 heteroatoms selected from the group consisting of O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, and a PEG group —(CH$_2$CH$_2$O)$_n$—R$^c$;

X' is independently selected from the group consisting of —H, —OH, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl, phenyl, and the amine-protecting group;

Y' is independently selected from the group consisting of —H, an oxo group, an optionally substituted linear C1-C10 alkyl, an optionally substituted branched C1-C10 alkyl, an optionally substituted cyclic C3-C10 alkyl, an optionally substituted linear C2-C10 alkenyl, an optionally substituted branched C2-C10 alkenyl, an optionally substituted cyclic C3-C10 alkenyl, an optionally substituted linear C2-C10 alkynyl, an optionally substituted branched C2-C10 alkynyl, an optionally substituted cyclic C3-C10 alkynyl; and the reminder of the variables are as defined for Formulas I-IV or first or second specific embodiment.

In a fourth specific embodiment, CM is represented by Formulas I-IV and XIII-XVI, wherein the double line ═ between N and C represents a single bond or a double bond, provided that when the double line ═ is a double bond, X is absent and Y is —H; and when the double line ═ is a single bond, X is —H and Y is selected from the group consisting of —H, —OR, —OCOR', —SR, —NR'R," —SO$_3$H, —SO$_2$H and —OSO$_3$H; X' is —H or -Me and Y' is —H or oxo; and, alternatively, X' and Y' are both —H; R, R', or R", for each occurrence, is independently —H, a linear C1-C4 alkyl, or a branched C1-C4 alkyl; and R$_6$ is —H, —R, —OR, or halogen. Alternatively, in Formulas I-IV and XIII-XVI, the double line ═ between N and C represents a single bond or a double bond, provided that when the double line ═ is a double bond, X is absent and Y is —H; and when the double line ═ is a single bond, X is —H and Y is selected from the group consisting of —H, —SO$_3$H, —OH, —OMe, —OEt and —NHOH. In another alternative, in Formulas I-IV and XIII-XVI, the double line ═ between N and C represents a single bond or a double bond, provided that when the double line ═ is a double bond, X is absent and Y is —H; and when the double line ═ is a single bond, X is —H and Y is —H, —SO$_3$H or —OH. The reminder of the variables are as defined for Formulas I-IV and XIII-XVI or the first, second or third specific embodiment.

In a fifth specific embodiment, CM is represented by Formulas I-IV, wherein W, when present, is C═O; and Z and Z', when present, are —CH$_2$—. The reminder of the variables are as defined for Formulas I-IV or first or second specific embodiment.

In a sixth specific embodiment, in Formulas I-IV and XIII-XVI, CM is represented by any one of the following formulas:

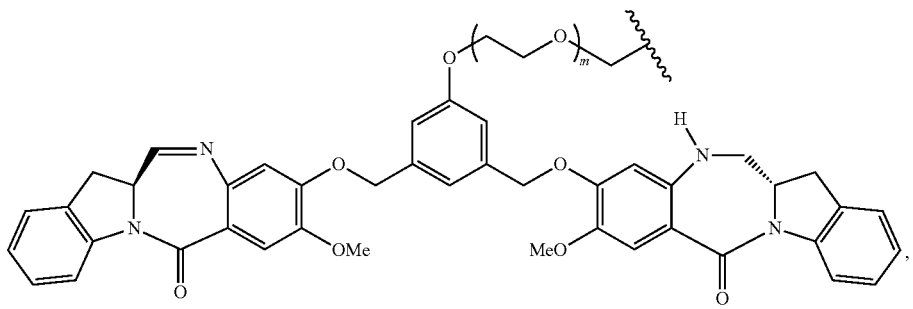

XVII

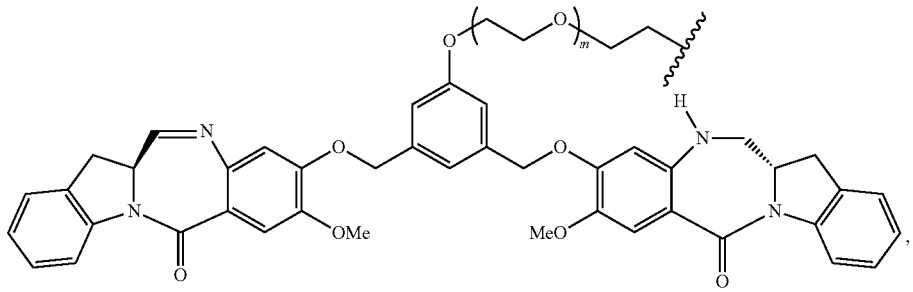

XVII'

-continued
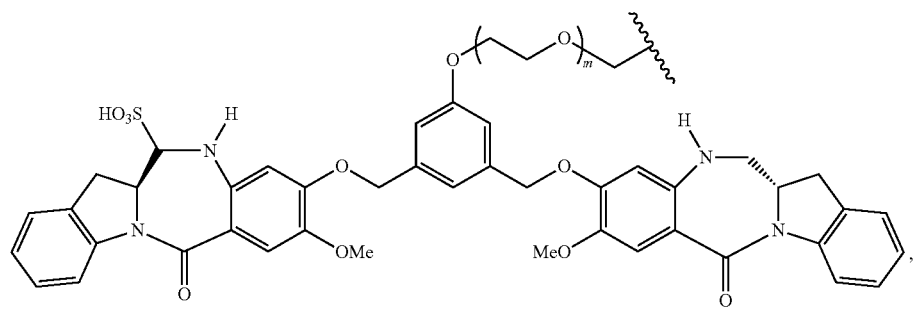
XVIII
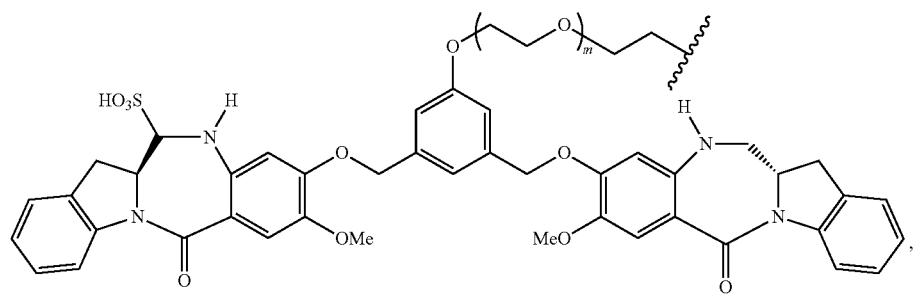
XVIII′
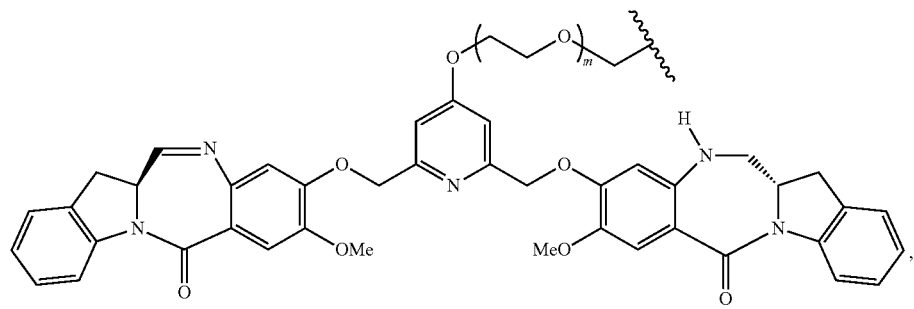
XIX
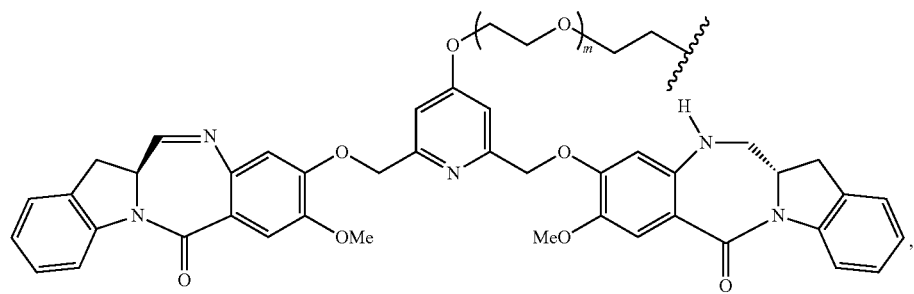
XIX′
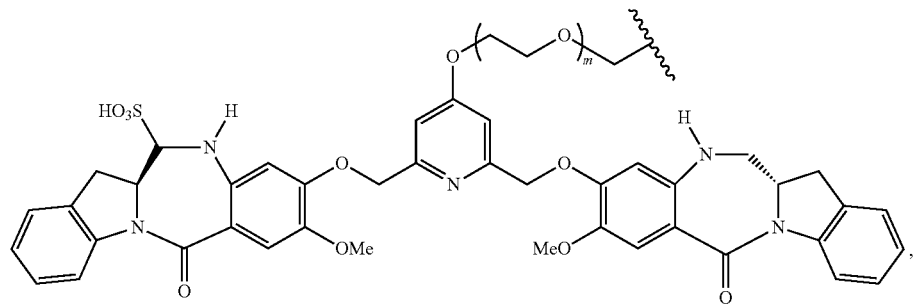
XX -continued
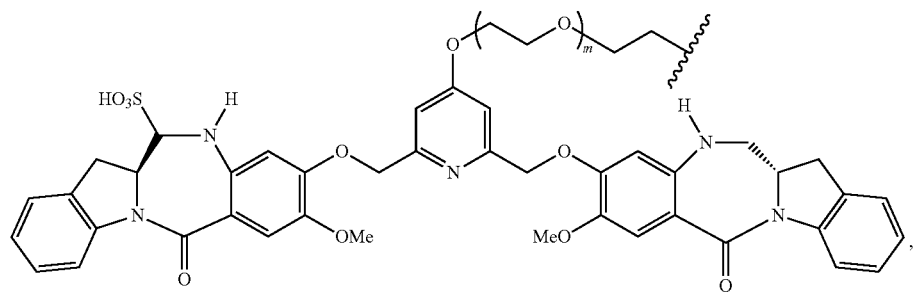
XX'
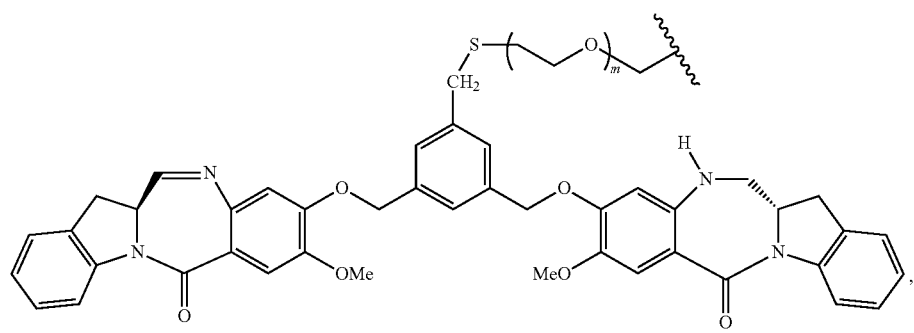
XXI
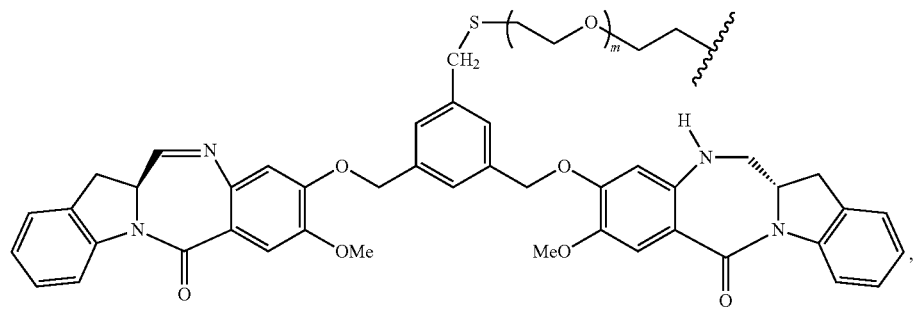
XXI'
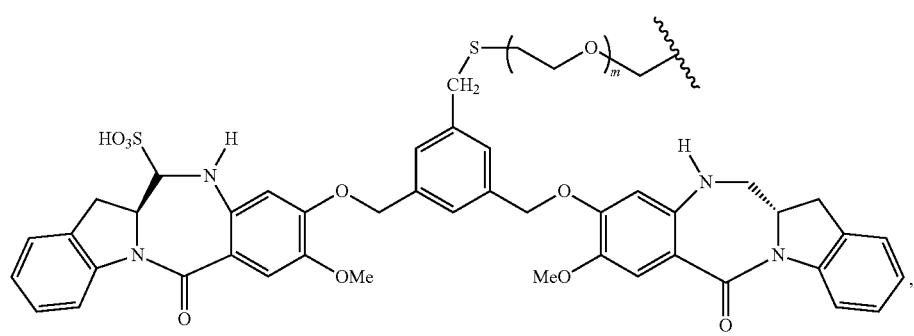
XXII
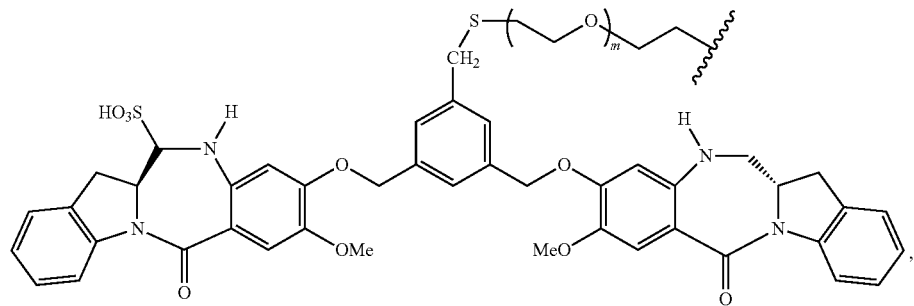
XXII'

-continued
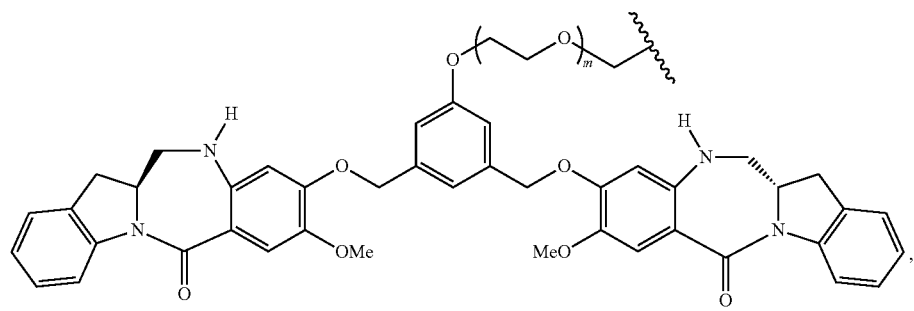
XXIII
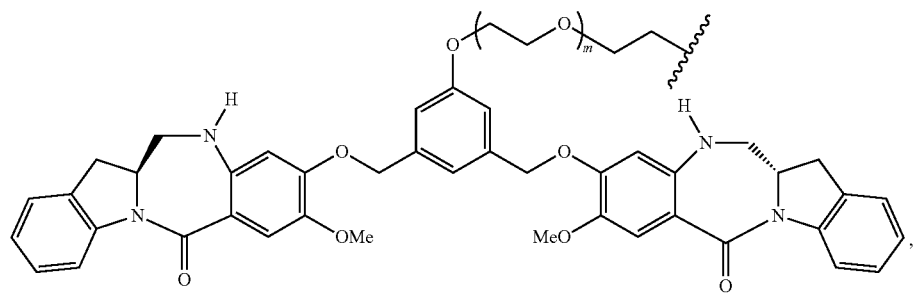
XXIII'
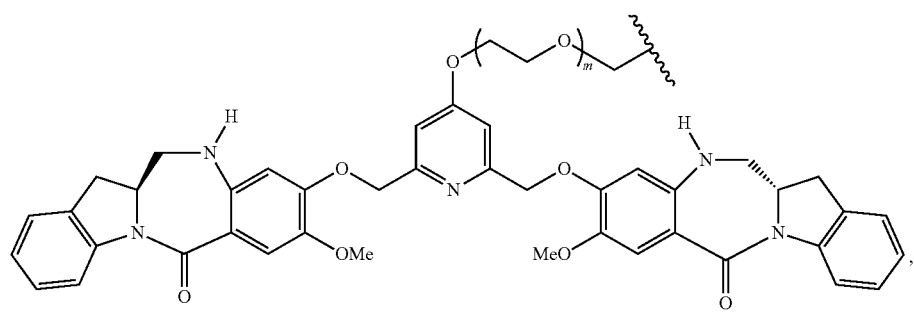
XXIV
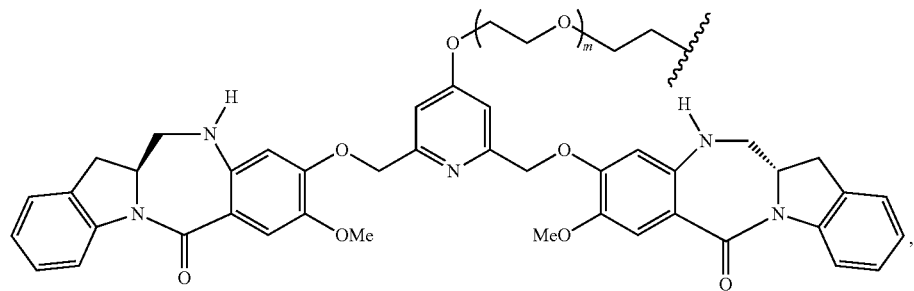
XXIV'
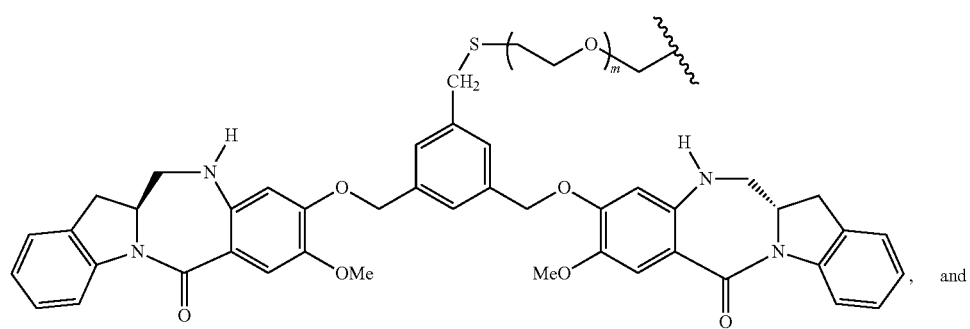
XXV
, and

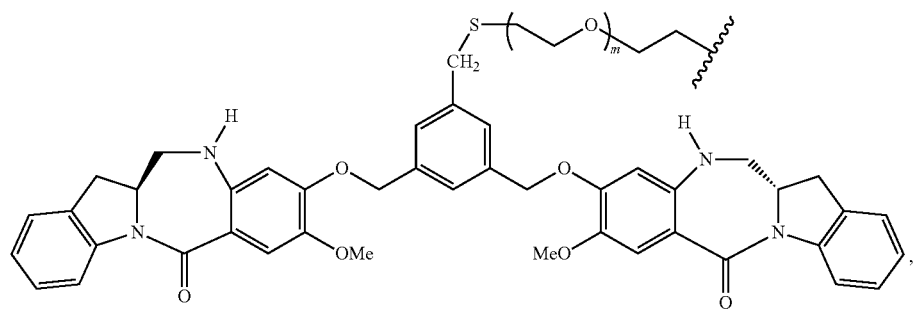

XXV' or a pharmaceutically acceptable salt thereof, wherein the variables are as defined for Formulas I-IV and XIII-XVI or the five specific embodiments described above. In one embodiment, the pharmaceutical acceptable salt of compounds of formula XVIII, XX and XXII is a sodium salt.

In a seventh specific embodiment, in Formula I, CM-Q is represented by the following formula:

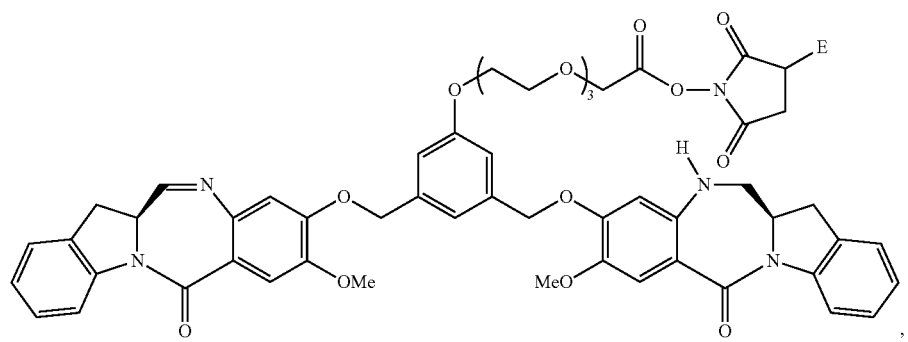

XXVI

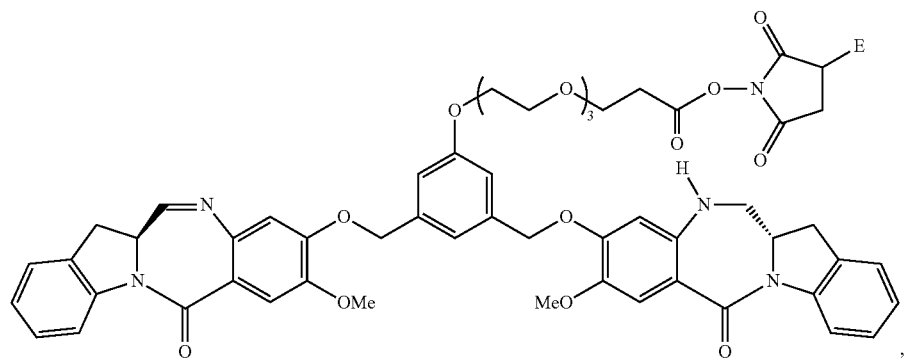

XXVI'

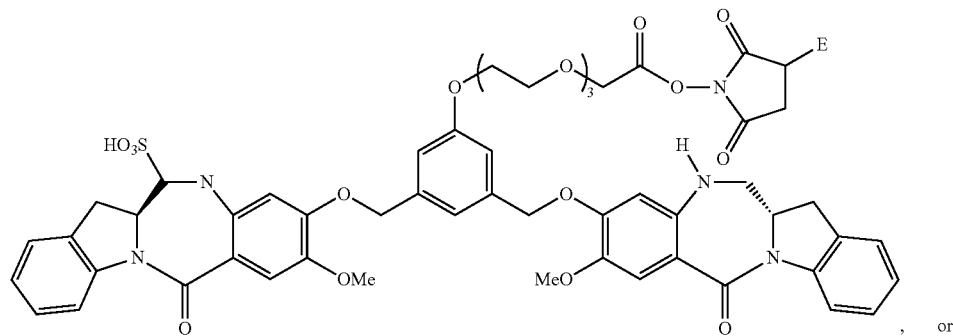

(XXVII)

, or

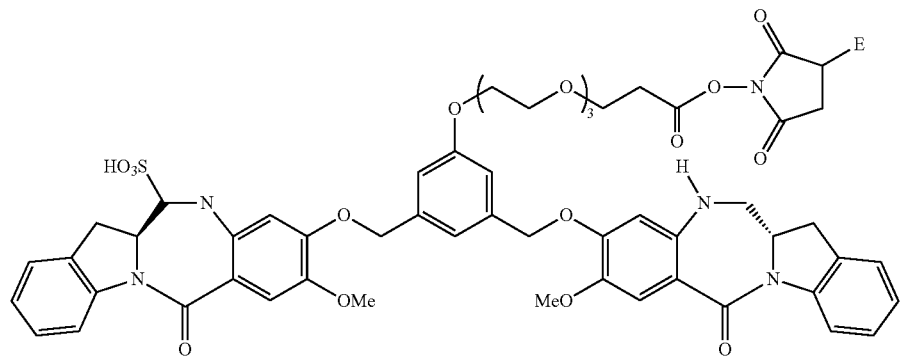

XXVII′ or a pharmaceutically acceptable salt thereof, wherein E is —H or —SO$_3$H. In one embodiment, the pharmaceutically acceptable salt for compound of formula (I) is a sodium salt.

In an eighth specific embodiment, CM is represented by Formulas I-IV and XIII-XXVII, wherein m, when present, is an integer from 1 to 10 and m is a range with the end values selected from any of 1-10 (e.g., 1-7, 3-6, etc.); alternatively, m is an integer of 1, 2, 3, 4, 5, 6, 7, 8, 9, or 10; and, in another alternative, m is 1, 2, 3, 4, 5, 6, 7; and the remainder of the variables are as defined for Formulas I-IV and XIII-XVI or the six specific embodiments described above.

Synthesis of Cytotoxic Compounds

Representative processes for preparing the cytotoxic compounds of the present invention are shown in FIGS. 1-6. A detail description of preparation of precursor Compound 1, including synthesis schemes, can be found in Example 29 of US 2010-0203007 A1 (incorporated herein by reference).

The synthesis of the other precursors, such as the ones listed below, can be similarly produced using substantially the same synthesis schemes.

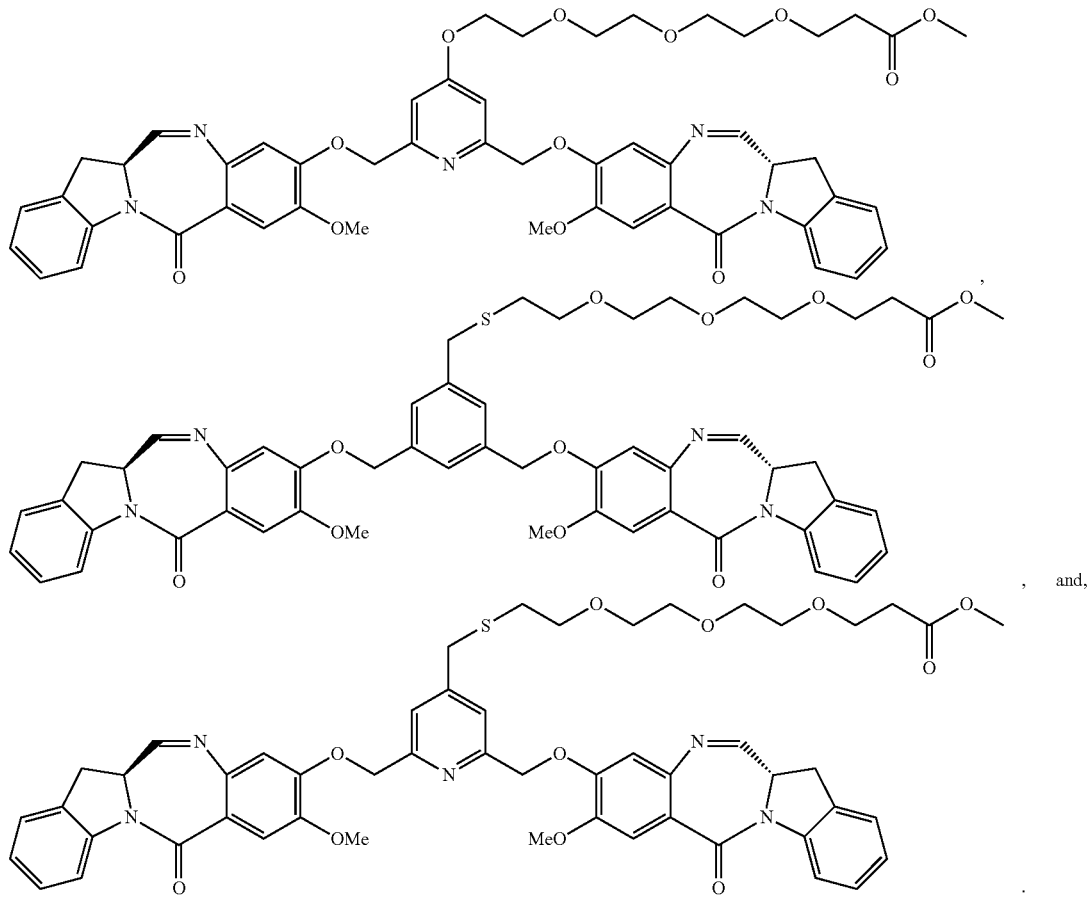

In particular, the synthesis schemes for two of the precursors above are provided in FIGS. 12-15.

These precursors can then be used in synthesis schemes similar to those in FIGS. 1-6.

Cell-Binding Agents

The effectiveness of the conjugates of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins (such as folate etc., which may bind to a cell surface receptor thereof, e.g., a folate receptor), nutrient-transport molecules (such as transferrin), or any other cell-binding molecule or substance.

In certain embodiments, the cell-binding agents are proteins or polypeptides, or compounds comprising proteins or polypeptides. Preferably, the proteins or polypeptides comprise one or more Lys residues with side chain —$NH_2$ groups. Alternatively or in addition, the proteins or polypeptides comprise one or more Cys residues. The side chain —SH groups of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains). In one embodiment, the cell-binding agent is a cysteine engineered antibodies, such as those described in U.S. Pat. No. 7,855,275. Alternatively, the cell-binding agents are proteins or polypeptides that comprise one or more unnatural amino acids, such as those described in US 2010/0184134, US 2010/0184135, US 2010/0048871, US 2010/0093082, US 2010/0167347 and U.S. Pat. No. 8,153,758, The Lys side chain —$NH_2$ groups and/or the Cys side chain —SH groups may be covalently linked to the linkers, which are in turn linked to the dimer compounds of the invention, thus conjugating the cell-binding agents to the dimer compounds of the invention. Each protein-based cell-binding agents may contain multiple Lys side chain —$NH_2$ groups and/or the Cys side chain —SH groups available for linking the compounds of the invention through the bifunctional crosslinkers.

More specific examples of cell-binding agents that can be used include:

antibodies, including polyclonal antibodies, monoclonal antibodies, fragments of antibodies, such as Fab, Fab', and F(ab')$_2$, Fv, minibodies, diabodies, tribodies, tetrabodies (Parham, *J. Immunol.* 131:2895-2902 (1983); Spring et al. *J. Immunol.* 113:470-478 (1974); Nisonoff et al. *Arch. Biochem. Biophys.* 89:230-244 (1960), Kim et al., *Mol. Cancer Ther.*, 7:2486-2497 (2008), Carter, *Nature Revs.*, 6:343-357 (2006));

interferons (e.g. α, β, γ);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, *Immunology Today* 5:155-158 (1984));

transferrin (O'Keefe et al., *J. Biol. Chem.* 260:932-937 (1985));

vitamins, such as folate;

Protein scaffolds based on a consensus sequence of fibronectin type III (FN3) repeats (also known as Centyrins; See U.S. Patent Publication 2010/0255056, incorporated herein by reference);

Designer Ankyrin Repeat Proteins (DARPins; U.S. Patent Application Nos. 20040132028; 20090082274; 20110118146; 20110224100, incorporated herein by reference), C. Zahnd et al. 2010, *Cancer Res.*, 70:1595-1605, incorporated herein by reference); and, Fibronectin domain scaffold proteins (Adnectins: US Patent Application Nos. 20070082365; 20080139791, incorporated herein by reference).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine IgG1 antibody that binds specifically to the CD33 Antigen (J. D. Griffin et al. *Leukemia Res.*, 8:521 (1984)) and can be used if the target cells express CD33 as in the disease of acute myelogenous leukemia (AML). The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that may be a polypeptide, or may be a transmembrane molecule (e.g. receptor for a ligand as described in the paragraph below). Alternatively, the cell-binding agent may be a ligand (such as a growth factor) or a functional portion thereof that binds to a cell surface molecule (such as a growth factor receptor). Thus by exploring the binding between antibody and antigen, or ligand and its receptor/target, the cell binding agent targets the conjugated drug molecule to a target cell bearing the antigen or the receptor/target.

Exemplary antigens or ligands include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance;

relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, melanotransferrin, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, tarnsferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, c-kit, 1GF1R, PSGR, NGEP, PSMA, PSCA, TMEFF2, LGR5, B7H4, and fragments of any of the above-listed polypeptides.

For example, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In one embodiment, the cell-binding agent is humanized monoclonal antibodies. In another embodiment, the cell-binding agent is huMy9-6, or other related antibodies, which are described in U.S. Pat. Nos. 7,342,110 and 7,557,189 (incorporated herein by reference). In another embodiment, the cell-binding agent is an anti-folate receptor antibody described in U.S. Provisional Application Nos. 61/307,797, 61/346,595, 61/413,172 and U.S. application Ser. No. 13/033,723 (published as US 2012-0009181 A1). The teachings of all these applications are incorporated herein by reference in its entirety.

In certain embodiments, the cell-binding agent may be a monoclonal antibody or antigen-binding portions thereof sharing sequences critical for antigen-binding with an antibody disclosed herein, such as huMy9-6 or its related antibodies described in U.S. Pat. Nos. 7,342,110 and 7,557,189 (incorporated herein by reference). These derivative antibodies may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody described herein. Sequences within these regions may contain conservative amino acid substitutions, including substitutions within the CDR regions. Preferably, there is no more than 1, 2, 3, 4, or 5 conservative substitutions. In certain embodiments, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the $K_d$ and/or $k_{off}$ values of the derivative antibodies are within 10-fold (either higher or lower), 5-fold (either higher or lower), 3-fold (either higher or lower), or 2-fold (either higher or lower) of an antibody described herein. These derivative antibodies may be fully human antibodies, or humanized antibodies, or chimeric antibodies. The derivative antibodies may be produced according to any art-recognized methods.

Cell-Binding Agent-Drug Conjugates

The present invention also provides cell-binding agent-drug conjugates comprising a CBA linked to one or more cytotoxic moieties described above. In one embodiment, the conjugate may be represented by any one of the following formulas:

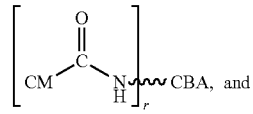

(IX)

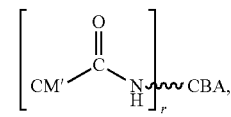

(X)

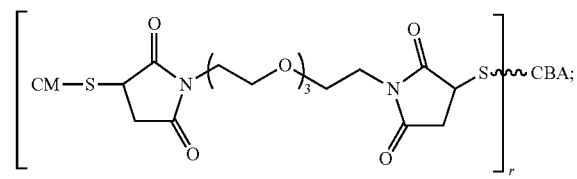

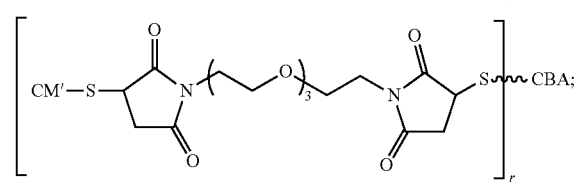

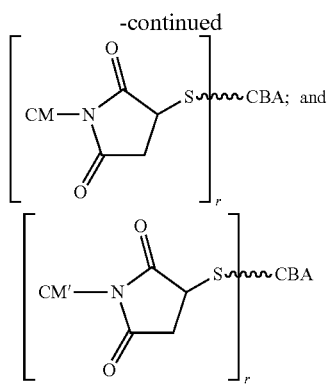

wherein CM is represented by any one of Formulas I-IV and XIII-XXVII, CM' is represented by any one of Formulas V-VII, and r is an integer from 1 to 10.

Examples of a conjugate include antibody/cytotoxic moiety, antibody fragment/cytotoxic moiety, epidermal growth factor (EGF)/cytotoxic moiety, melanocyte stimulating hormone (MSH)/cytotoxic moiety, thyroid stimulating hormone (TSH)/cytotoxic moiety, somatostatin/cytotoxic moiety, folate/cytotoxic moiety, estrogen/cytotoxic moiety, estrogen analogue/cytotoxic moiety, prostate specific membrane antigen inhibitor/cytotoxic moiety, matriptase inhibitor/cytotoxic moiety, designed ankyrin repeat proteins/cytotoxic moiety, androgen/cytotoxic moiety, and androgen analogue/cytotoxic moiety. A representative synthesis scheme for the conjugate is shown in FIG. 7.

The covalent linker between a CBA and CM or CM' can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

In one embodiment, a conjugate comprises CM is represented by any one of Formulas XIII-XXVI.

In certain embodiments, the conjugates described above may each comprise 1-10 cytotoxic moieties, 2-9 cytotoxic moieties, 3-8 cytotoxic moieties, 4-7 cytotoxic moieties, or 5-6 cytotoxic moieties. In other words, r can be an integer from 1 to 10, 2 to 9, 2 to 8, 2 to 7, 2 to 6, or 2-5.

In certain embodiments, the cell-binding agent specifically binds to target cells selected from tumor cells, virus infected cells, microorganism infected cells, parasite infected cells, autoimmune cells, activated cells, myeloid cells, activated T-cells, B cells, melanocytes, cells expressing CD4, CD6, CD19, CD20, CD22, CD30, CD33, CD37, CD38, CD40, CD44, CD56, EpCAM, CanAg, CALLA, Her-2 antigens, Her-3 antigens, insulin growth factor receptor, epidermal growth factor receptor, or folate receptor.

In certain embodiments, the CBA is an antibody, a single chain antibody, an antibody fragment, a polycloncal antibody, a monoclonal antibody, a single chain monoclonal antibody, a monoclonal antibody fragment, a chimeric antibody, a chimeric antibody fragment, a domain antibody, a domain antibody fragment, a lymphokine, a hormone, a vitamin, a growth factor, a colony stimulating factor, or a nutrient-transport molecule. The CBA preferably binds to a target on the cell (e.g., a cell surface receptor or a cell surface antigen or a cell surface molecule) specifically.

In certain embodiments, the CBA is a resurfaced antibody, a resurfaced single chain antibody, or a resurfaced antibody fragment.

In certain embodiments, the CBA is a polyclonal antibody.

In certain embodiments, the CBA is a monoclonal antibody, a single chain monoclonal antibody, or a monoclonal antibody fragment thereof.

In certain embodiments, the CBA is a humanized antibody, a humanized single chain antibody, or a humanized antibody fragment.

In certain embodiments, the conjugates described above do not include the conjugate having a cytotoxic moiety represented by Formula XII.

Production of Cell-Binding Agent-Drug Conjugates

In order to link a cytotoxic moiety of the present invention to a CBA, the cytotoxic compounds described above comprise a reactive group, which react with the CBA. Examples of the reactive group include a maleimide, a haloacetamido, —SH, —SSR$^d$, —CH$_2$SH, —CH(Me)SH, —C(Me)$_2$SH, —NHR$^{c1}$, —CH$_2$NHR$^{c1}$, —NR$^{c1}$NH$_2$, —COOH, and —COE, wherein —COE represents a reactive ester selected from, but not limited to, N-hydroxysuccinimide ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester, and wherein R$^{c1}$ is —H or a substituted or unsubstituted linear or branched alkyl having 1 to 4 carbon atoms, and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl), wherein R$^{c1}$ is —H or a substituted or unsubstituted linear or branched alkyl having 1 to 4 carbon atoms, and R$^d$ is selected from the group consisting of phenyl, nitrophenyl, dinitrophenyl, carboxynitrophenyl, pyridyl and nitropyridyl.

A representative process for preparing the cell-binding agent-drug conjugates of the present invention is shown in FIG. 7. The cytotoxic compounds described above can be conjugated with a CBA through a one-step conjugation method. In FIG. 7, representative examples are described, wherein three compounds each terminating in an N-hydroxysuccinimide ester is reacted directly with a cell binding agent, such as an antibody, generating the desired conjugate. In FIG. 7, the cytotoxic compounds were directly treated with an antibody.

The cell binding agent-drug conjugate may then be purified using any purification methods known in the art, such as those described in U.S. Pat. No. 7,811,572 and US Publication No. 2006/0182750, both of which are incorporated herein by reference. For example, the cell-binding agent-drug conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

The number of cytotoxic molecules bound per antibody molecule can be determined spectrophotometrically by measuring the ratio of the absorbance at 280 nm and 330 nm. An average of 1-10 cytotoxic compounds/antibody molecule(s) can be linked by the methods described herein. The preferred average number of linked cytotoxic compounds per antibody molecule is 2-5, and the most preferred is 2.5-4.0.

Processes for synthesizing the conjugates and precursors of the invention are also described in U.S. provisional patent application Nos. 61/443,092 and 61/443,062, both filed on Feb. 15, 2011, U.S. provisional patent application No.

61/483,499, filed on May 6, 2011, and U.S. utility application Ser. Nos. 13/397,205 and 13/397,195 (filed on Feb. 15, 2012), the entire contents of which applications, including all drawings, formulae, synthesis schemes, specifications, and claims, are incorporated herein by reference.

In Vitro Cytotoxicity of Compounds and Conjugates

The cytotoxic compounds and conjugates thereof of the invention can be evaluated for their ability to suppress proliferation of various cancer cell lines in vitro. For example, cell lines such as the human colon carcinoma line COLO 205, the rhabdomyosarcoma cell line RH-30, the multiple myeloma cell line MOLP-8, as well as the Namalwa, KB, NB4, HEL92.1.7, and HL60/QC cell lines used in FIGS. 8-11, can all be used for the assessment of cytotoxicity of these compounds and conjugates.

Methods useful for the assessment of cytotoxicity of these compounds and conjugates are known in the art. For example, U.S. Ser. No. 13/397,195, filed on Feb. 15, 2012, describes detailed experimental protocols for assessing cytotoxicity of benzodiazepine compounds and conjugates. See, for example, Examples 7-10, 15, 25, 30, and 31, the entire contents of which is incorporated herein by reference.

In general, cells to be evaluated (such as the cells used in the experiments pertaining to the figures) can be exposed to the compounds or conjugates for 1-5 days and the surviving fractions of cells measured in direct assays by known methods. $IC_{50}$ values can then be calculated from the results of the assays. Alternatively or in addition, an in vitro cell line sensitivity screen, such as the one described by the U.S. National Cancer Institute (see Voskoglou-Nomikos et al., 2003, *Clinical Cancer Res.* 9:4227-4239, incorporated herein by reference) can be used as one of the guides to determine the types of cancers that may be sensitive to treatment with the compounds or conjugates of the invention.

Examples of in vitro potency and target specificity of antibody-cytotoxic moiety conjugates of the present invention are shown in FIGS. 8-11. All of the conjugates are extremely cytotoxic on the antigen positive cancer cells with an IC50 in the low picomolar range.

Figure 10A:
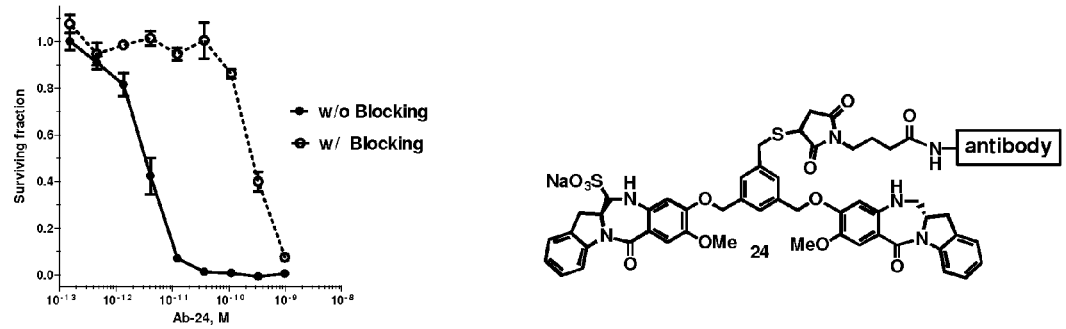
Figure 10B:
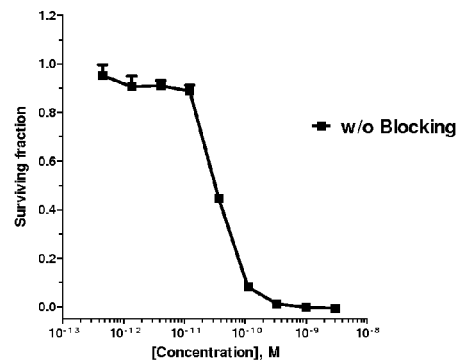
Figure 10C:
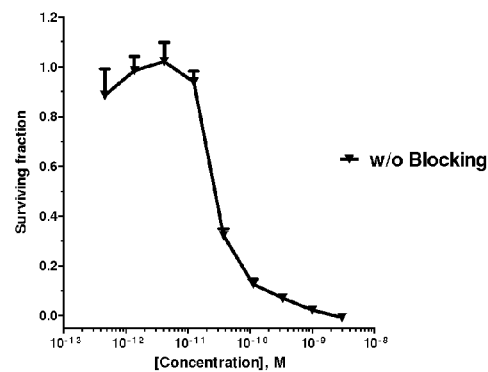
Figure 11A:
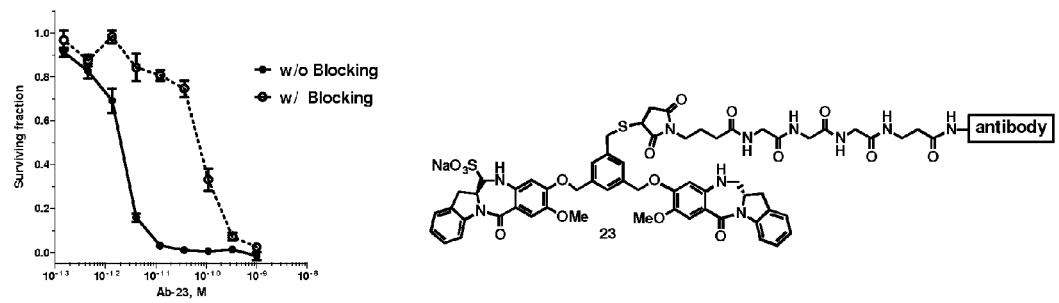
FIGS. 11A, 11B and 11C show the in vitro antiproliferative activity of conjugate 23 against cell lines HL60/QC (with or without the blocking antigen binding site), NB4 (without the blocking antigen binding site) and HEL92.1.7 (without the blocking antigen binding site), respectively.
Figure 11B:
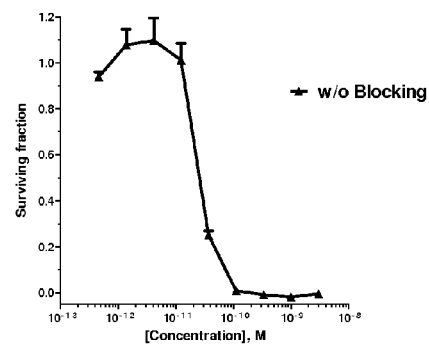
Figure 11C:
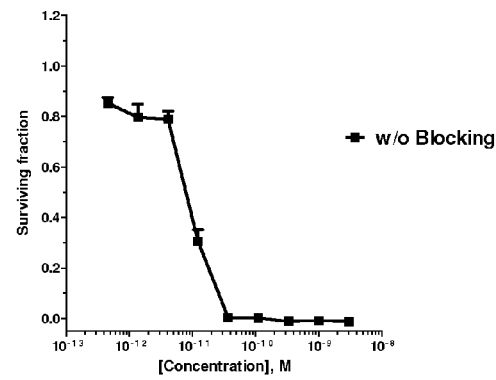

The benzodiazepine compounds showed target specific potency being substantially less potent when blocked with unconjugated antibody. Conjugate 22 killed antigen positive HL60/QC cells with an $IC_{50}$ value of 1.8 pM, while the addition of an excess of unconjugated huMy9-6 antibody reduced this cytotoxic effect ($IC_{50}$>1 nM), demonstrating antigen specificity (FIG. 9A). In addition, conjugates 23 and 24 are also highly potent towards HL60/ATCC cell line with $IC_{50}$ values of 2.0 pM and 3.1 pM, respectively (FIGS. 10 and 11).

Compositions and Methods of Use

In one aspect, the present invention includes a composition (e.g., a pharmaceutical composition) comprising a cytotoxic compound described herein (e.g., benzodiazepine), a derivative thereof, or a conjugate thereof, (and/or a solvate, a hydrate and/or a salt thereof) and a carrier (a pharmaceutically acceptable carrier). The composition can further comprise a second therapeutic agent.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

In another aspect, the present invention provides a method for inducing cell death in selected cell populations comprising contacting target cells or tissue containing target cells with an effective amount of a conjugate comprising any of the cytotoxic compound-cell-binding agents of the present invention, a salt or solvate thereof. The target cells are cells to which the cell-binding agent can bind.

In yet another aspect, the present invention includes a method of inhibiting abnormal cell growth or treating a proliferative disorder (e.g., cancer) in a mammal comprising administering to said mammal a therapeutically effective amount of a composition containing a cytotoxic compounds described herein, derivatives thereof, conjugates thereof, solvates thereof, and salts thereof.

The cancer is selected from the group consisting of breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, non-small cell lung cancer, testicular cancer, Merkel cell carcinoma, glioblastoma, neuroblastoma, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin's lymphomas (Nodular sclerosis, Mixed cellularity, Lymphocyte-rich, Lymphocyte depleted or not depleted, and Nodular lymphocyte-predominant Hodgkin lymphoma), Non-Hodgkin's lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler's disease).

If desired, other active agents, such as other anti-tumor agents, may be administered along with the conjugate. In one embodiment, the other anti-tumor agent is selected from the group consisting of bortezomib, revlimid, paclitaxel, docetaxel, cisplatin, carboplatin, doxorubicin, vinblastine, rituximab, alemtuzumab, trastuzumab, cetuximab, panitumumab and bevacizumab.

This method is also useful for treating an autoimmune disorder (e.g., rheumatoid arthritis, multiple sclerosis, and systemic lupus), transplant rejection (graft versus host disease, renal transplant rejection, liver transplant rejection, lung transplant rejection, cardiac transplant rejection, and bone marrow transplant rejection), immune deficiency, inflammatory diseases (e.g., myositis and pancreatitis), destructive bone disorder, infectious disease, parasite infections (e.g., giardiasis, amoebiasis, and schistosomiasis), viral disease (e.g., CMV infection, HIV infection, and AIDS), fibrotic disease, neurodegenerative disorder, kidney disease, depression, anxiety, stress, phobias, panic, dysphoria, psychiatric disorders, or pain in a mammal.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

In certain embodiments, a second chemotherapeutic agent is administered to the mammal sequentially or consecutively. In one embodiment, the second chemotherapeutic agent is selected from the group consisting of bortezomib, revlimid, paclitaxel, docetaxel, cisplatin, carboplatin, doxorubicin, vinblastine, rituximab, alemtuzumab, trastuzumab, cetuximab, panitumumab and bevacizumab.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 µg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index

By Manufacturer

Products (by company's or trademarked drug name)

Category index

Generic/chemical index (non-trademark common drug names)

Color images of medications

Product information, consistent with FDA labeling

Chemical information

Function/action

Indications & Contraindications

Trial research, side effects, warnings

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument and mass spectra were acquired on a Bruker Daltonics Esquire 3000 instrument using electrospray ionization.

Example 1

Preparation of Compound 5

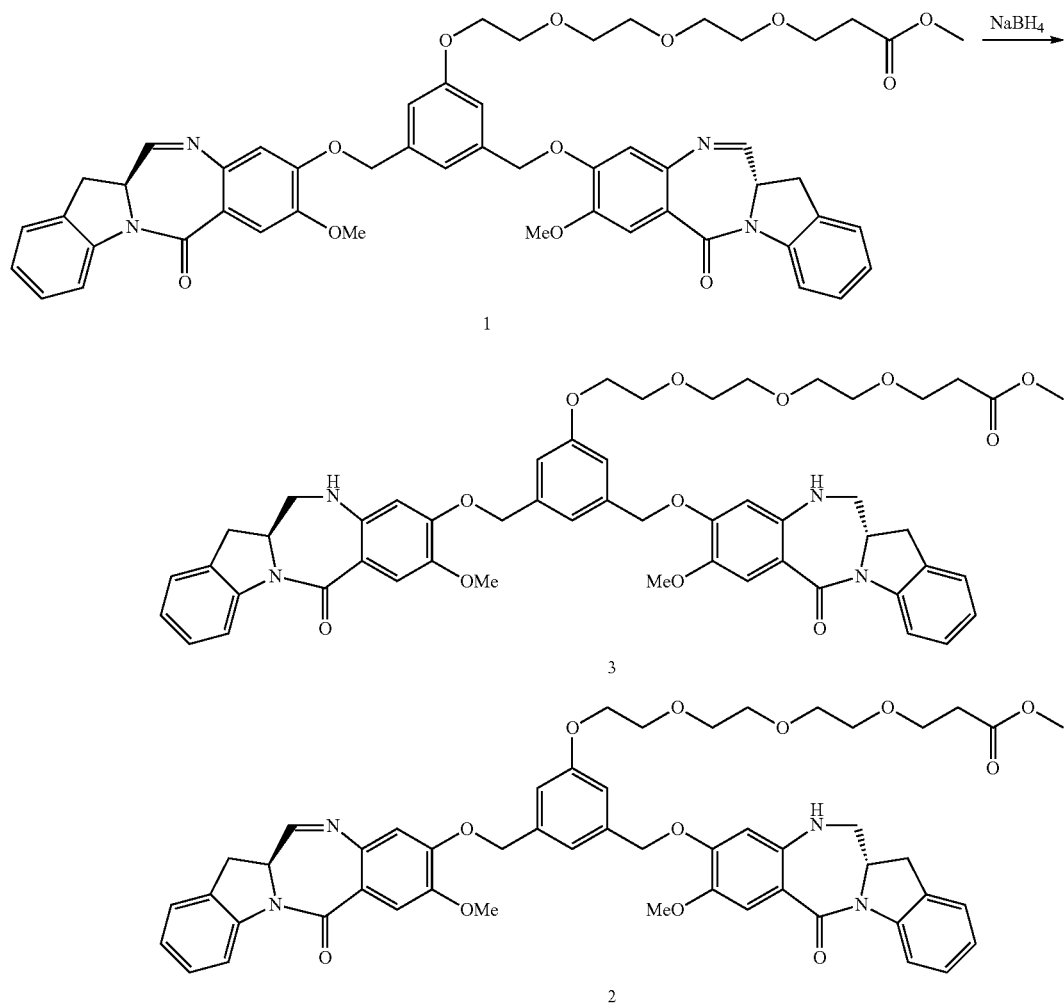

Compound 1 (164 mg, 75% purity, 0.133 mmol) was dissolved in absolute ethanol (1.0 ml) and anhydrous dichloromethane (0.67 ml). The solution was cooled to 0° C. in an ice bath and sodium borohydride (2.52 mg, 0.066 mmol) was added resulting in a bright yellow solution. The reaction was stirred at 0° C. for 5 minutes and then at room temperature for 3 hours. The reaction was then cooled to 0° C. in an ice bath, quenched with saturated ammonium chloride and diluted with dichloromethane. The organic layer was washed with brine, dried over sodium sulfate and filtered through celite. The filtrate was evaporated under reduced pressure and the crude residue purified by RP-HPLC (C18 DI Water/Acetonitrile) to yield compound 2 (26 mg, 96% pure, y=20%).) MS (m/z) found, 967.1 (M+Na+ $H_2O$).

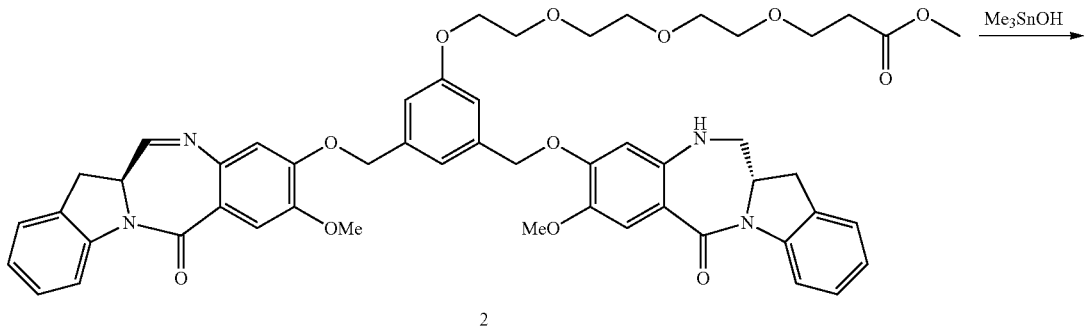

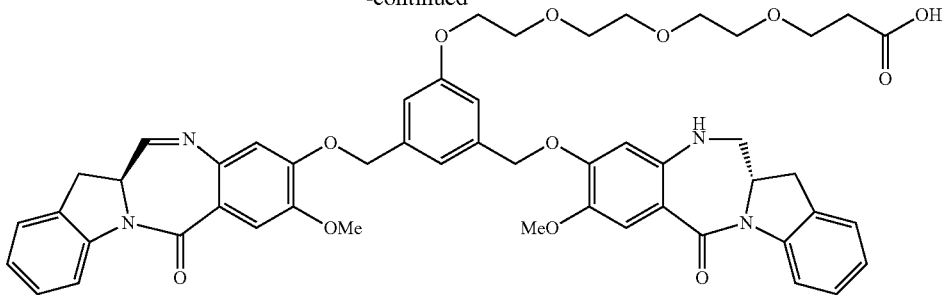

4

Compound 2 (69 mg, 0.058 mmol) was dissolved in anhydrous 1,2-dichloroethane (5.8 mL) and trimethyl tin hydroxide (210 mg, 1.161 mmol) was added. After refluxing overnight the mixture was cooled to room temperature and diluted with dichloromethane. The organic layer was washed with brine containing a few drops of 5% HCl and then brine alone. The organic layer was then dried over anhydrous sodium sulfate and filtered. The filtrate was concentrated under reduced pressure and purified by silica gel chromatography (neat dichloromethane→5% methanol in dichloromethane) to give compound 4. (25.5 mg, 78% purity, y=37.5%). MS (m/z) found, 935.5 (M+Na) and 911.4 (M−H).

filtrate was evaporated under reduced pressure and the crude material was purified by RP-HPLC (C18 DI Water/Acetonitrile) to yield the final compound 5 (9.1 mg, y=42%). MS (m/z) found, 1050.5 (M+Na+H2O).

Example 2

Preparation of Conjugate 22 from Compound 5 and huMy9-6

As shown in FIG. 7, a reaction containing 2.0 mg/mL huMy9-6 antibody and 5 molar equivalents compound 5 (pretreated with 5-fold excess of sodium bisulfite in 90:10

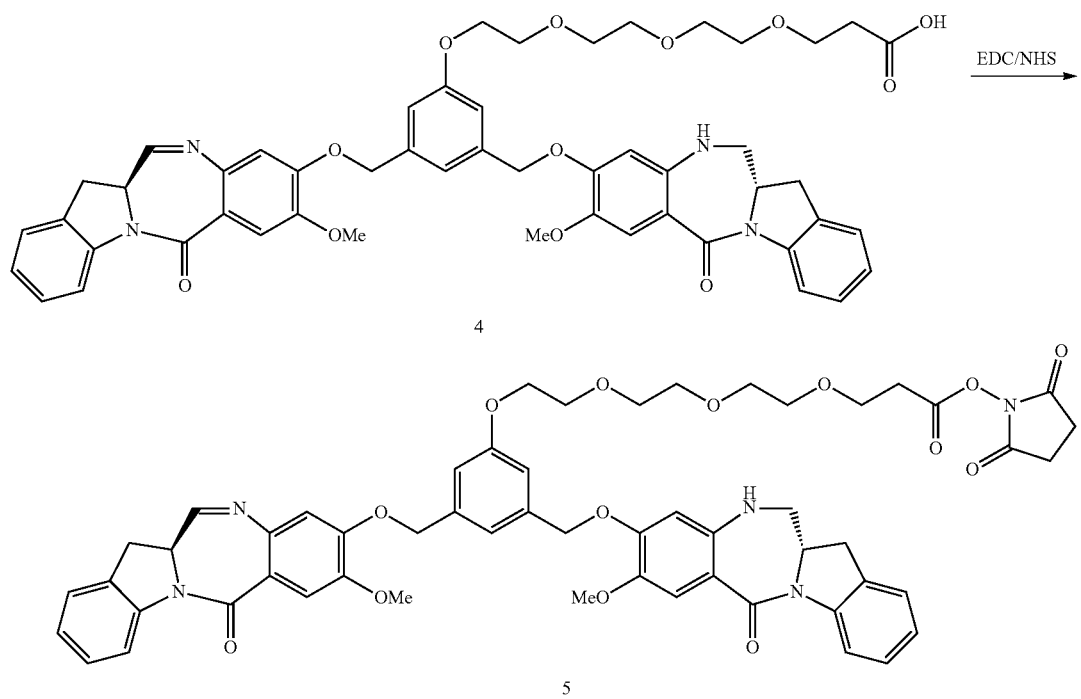

Compound 4 (25 mg, 78% purity, 0.021 mmol) was dissolved in anhydrous dichloromethane (0.75 mL) and cooled to 0° C. in and ice bath. N-hydroxy succinimide (7.37 mg, 0.064 mmol) and EDC.HCl (12.28 mg, 0.064 mmol) were added and the resulting mixture was stirred at 0° C. for 30 minutes and then overnight at room temperature. The reaction was diluted with dichloromethane, washed with brine, dried over anhydrous sodium sulfate and filtered. The DMA:water) in 50 mM HEPES (4-(2-hydroxyethyl)-1-piperazine ethanesulfonic acid) pH 8.5 buffer and 10% v/v DMA (N,N-Dimethylacetamide) cosolvent was allowed to conjugate for 4 hours at 25° C.

Post-reaction, the conjugate was purified and buffer exchanged into 250 mM Glycine, 10 mM Histidine, 1% sucrose, 0.01% Tween-20, 50 μM sodium bisulfite formulation buffer pH 6.2 using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO).

The purified conjugate was found to have an average of 3.4 compound 5 linked per antibody (by UV-Vis using molar extinction coefficients $\epsilon_{330\ nm}$=15,280 cm$^{-1}$M$^{-1}$ and $\epsilon_{280\ nm}$=30, 115 cm$^{-1}$M$^{-1}$ for compound 5, and $\epsilon_{280\ nm}$=207,000 cm$^{-1}$M$^{-1}$ for My9-6 antibody), 98% monomer (by size exclusion chromatography), <0.2% unconjugated compound 5 (by dual-column reverse-phase HPLC analysis) and a final protein concentration of 1.5 mg/ml.

Example 3

Preparation of Conjugate 23 from Compound 19 and huMy9-6

As shown in FIG. 6, 1.5 mM CX1-1 linker (compound 20) was mixed with 2 mM compound 18 (free thiol) and 10 mM DIPEA (diisopropylethylamine) in DMA (N,N-Dimethylacetamide) for 10 min at rt. 1 mM MPA (3-maleimido propionic acid) was then added to react with the excess compound 18 for 5 min. As shown in FIG. 7, the resultant compound, i.e., compound 19, (5 molar equivalents per antibody based on CX1-1-linker) was added to a 2.0 mg/mL huMy9-6 antibody solution buffered in 50 mM HEPES (4-(2-hydroxyethyl)-1-piperazine ethanesulfonic acid) pH 8.5 and 10% v/v DMA (N,N-Dimethylacetamide) cosolvent, and allowed to react for 4 hours at 25° C.

Post-reaction, the conjugate was purified and buffer exchanged into 250 mM Glycine, 10 mM Histidine, 1% sucrose, 0.01% Tween-20, 50 μM sodium bisulfite formulation buffer pH 6.2 using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO).

The purified conjugate was found to have an average of 3.3 compound 18 linked per antibody (by UV-Vis using molar extinction coefficients $\epsilon_{330\ nm}$=15,484 cm$^{-1}$M$^{-1}$ and $\epsilon_{280\ nm}$=30, 115 cm$^{-1}$M$^{-1}$ for compound 18, and $\epsilon_{280\ nm}$=207,000 cm$^{-1}$M$^{-1}$ for My9-6 antibody), 97% monomer (by size exclusion chromatography), <0.2% unconjugated compound 18 (by dual-column reverse-phase HPLC analysis) and a final protein concentration of 0.9 mg/ml.

Example 4

Preparation of Conjugate 24 from Compound 21 and huMy9-6

As shown in FIG. 6, 1.5 mM sulfoNHS-GMBS linker (Pierce, Co) was mixed with 2 mM compound 18 (free thiol) and 10 mM DIPEA (diisopropylethylamine) in DMA (N,N-Dimethylacetamide) for 15 min at rt. 2 mM MPA (3-maleimido propionic acid) was then added to react with the excess compound 18 for 5 min. As shown in FIG. 7, the resultant compound, i.e., compound 21, (5.5 molar equivalents per antibody based on GMBS linker) was added to a 2.0 mg/mL huMy9-6 antibody solution in 50 mM HEPES (4-(2-hydroxyethyl)-1-piperazine ethanesulfonic acid) pH 8.5 buffer and 15% v/v DMA (N,N-Dimethylacetamide) cosolvent, and allowed to react for 4 hours at 25° C.

Post-reaction, the conjugate was purified and buffer exchanged into 250 mM Glycine, 10 mM Histidine, 1% sucrose, 0.01% Tween-20, 50 μM sodium bisulfite formulation buffer pH 6.2 using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO).

The purified conjugate was found to have an average of 2.9 compound 18 linked per antibody (by UV-Vis using molar extinction coefficients 8330 nm=15,484 cm-1M-1 and 8280 nm=30, 115 cm-1M-1 for compound 18, and 8280 nm=207,000 cm-1M-1 for My9-6 antibody), 96% monomer (by size exclusion chromatography), <0.2% unconjugated compound 18 (by dual-column reverse-phase HPLC analysis) and a final protein concentration of 0.6 mg/ml.

We claim:

1. A cytotoxic compound represented by CM-Q, wherein CM is a cytotoxic moiety represented by the following formula:

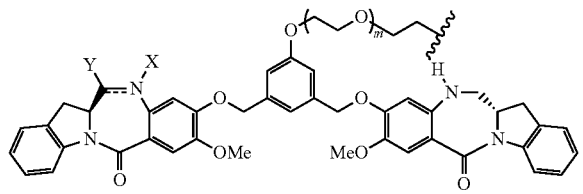

or a pharmaceutically acceptable salt thereof, wherein:

Q is —COOR$^c$, or —COE, wherein —COE represents a reactive ester selected from the group consisting of N-hydroxysuccinimide ester, N-hydroxy sulfosuccinimide ester, nitrophenyl ester, dinitrophenyl ester, sulfo-tetrafluorophenyl ester, and pentafluorophenyl ester;

the double line $=\!=$ between N and C represents a single bond or a double bond, provided that when the double line $=\!=$ is a double bond, X is absent and Y is —H; and when the double line $=\!=$ is a single bond, X is —H and Y is —SO$_3$H or —OH;

R$^c$ is —H, a linear C1-C4 alkyl or a branched C1-C4 alkyl; and, m is an integer from 1 to 24.

2. The compound of claim 1, wherein Q is —C(=O)OH, —C(=O)OMe, or

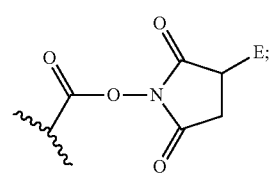

and E is —H or —SO$_3$H.

3. The compound of claim 1, wherein CM is represented by any one of the following formulas:

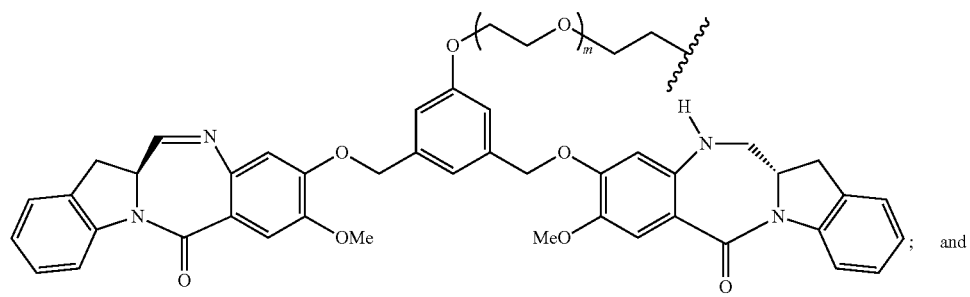
; and
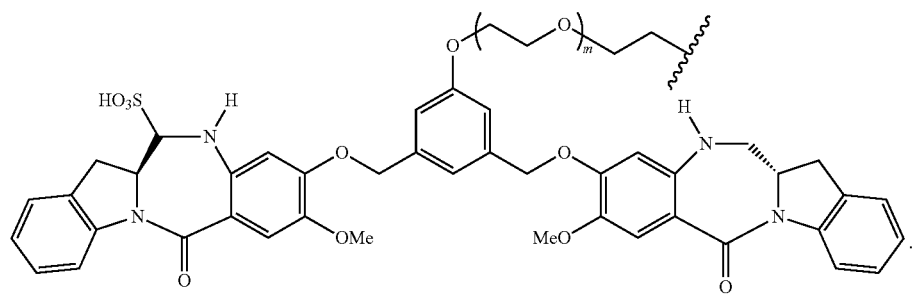
.
4. The compound of claim 1, wherein CM-Q is represented by the following formula:
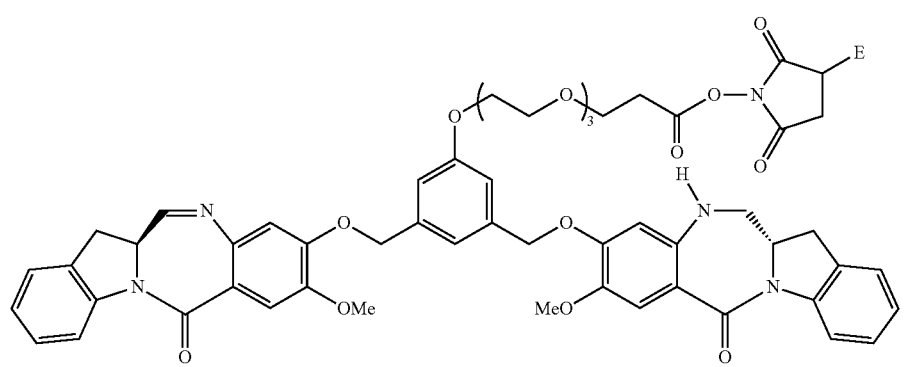
wherein E is —H or —SO$_3$H.
5. A conjugate comprising a cytotoxic moiety and a CBA, wherein the conjugate is represented by the following formula:
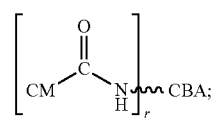

and wherein the cytototoxic moiety is CM in claim 1, CBA〰️N—H— represents a cell-binding agent covalently linked to the cytotoxic moiety, the cell-binding agent is an antibody or an antibody fragment; and r is an integer from 1 to 10, provided that CM is not

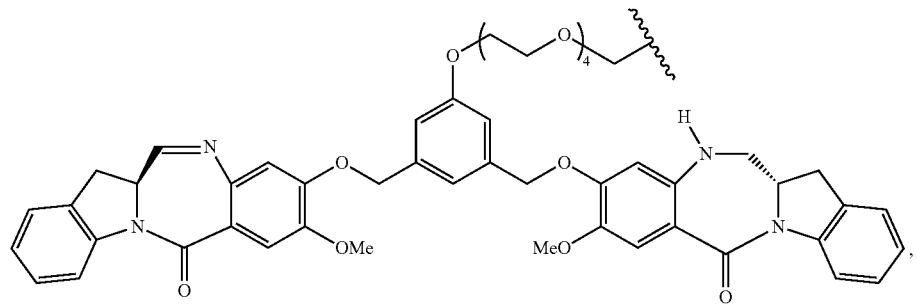

and/or a salt thereof.

6. A pharmaceutical composition comprising the conjugate of claim 5; and a pharmaceutically acceptable carrier.

7. The compound of claim 1, wherein m is an integer from 1 to 10.

8. The conjugate of claim 5, wherein m is an integer from 1 to 10.

9. The conjugate of claim 5, wherein the CBA is a resurfaced antibody, a resurfaced single chain antibody, or a resurfaced antibody fragment.

10. The conjugate of claim 5, wherein the CBA is a monoclonal antibody, a single chain monoclonal antibody, or a monoclonal antibody fragment thereof.

11. The conjugate of claim 5, wherein the CBA is a humanized antibody, a humanized single chain antibody, or a humanized antibody fragment.

12. The conjugate of claim 5, wherein the CBA is huMy9-6, huFOLR1, or chB38.1.

13. The conjugate of claim 5, wherein CM is represented by the following formula:

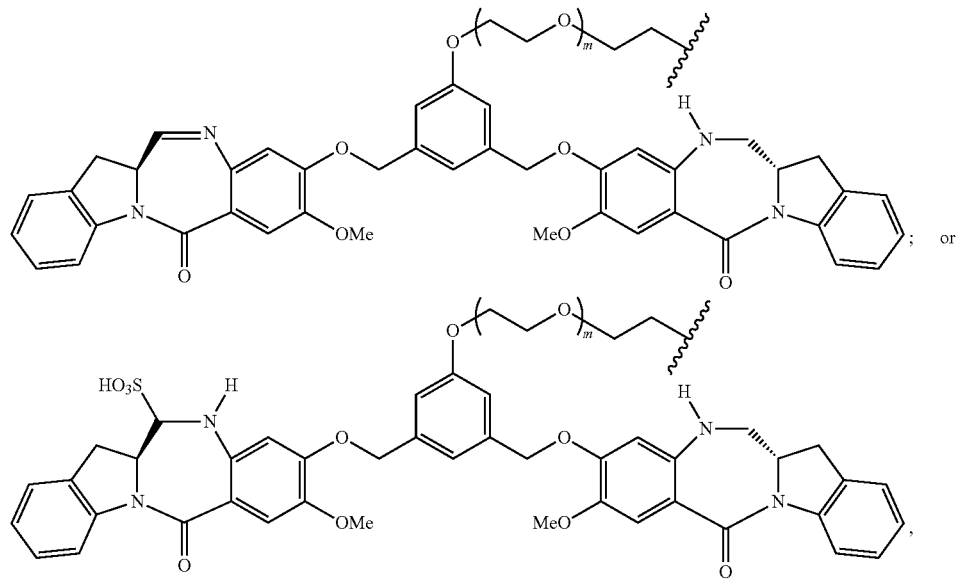

or a pharmaceutically acceptable salt thereof.

* * * * *